US012807694B2

(12) United States Patent
Xu et al.

(10) Patent No.: US 12,807,694 B2
(45) Date of Patent: Nov. 24, 2026

(54) ANTI-ANGPTL3 ANTIBODY OR ANTIGEN-BINDING FRAGMENT THEREOF, AND PREPARATION METHOD AND USE THEREOF

(71) Applicant: CHILDREN'S HOSPITAL OF FUDAN UNIVERSITY, Shanghai (CN)

(72) Inventors: Hong Xu, Shanghai (CN); Qian Shen, Shanghai (CN); Jia Rao, Shanghai (CN); Yihui Zhai, Shanghai (CN); Li Sun, Shanghai (CN); Haimei Liu, Shanghai (CN); Qianying Lv, Shanghai (CN); Xinli Han, Shanghai (CN)

(73) Assignee: Children's Hospital of Fudan University, Shanghai (CN)

( * ) Notice: Subject to any disclaimer, the term of this patent is extended or adjusted under 35 U.S.C. 154(b) by 435 days.

(21) Appl. No.: 18/039,251

(22) PCT Filed: Mar. 30, 2021

(86) PCT No.: PCT/CN2021/084206
§ 371 (c)(1),
(2) Date: May 29, 2023

(87) PCT Pub. No.: WO2022/205021
PCT Pub. Date: Oct. 6, 2022

(65) Prior Publication Data
US 2024/0092884 A1 Mar. 21, 2024

(51) Int. Cl.

| | |
|---|---|
| ***C07K 16/22*** | (2006.01) |
| ***A61K 39/00*** | (2006.01) |
| ***A61P 3/06*** | (2006.01) |
| ***A61P 7/00*** | (2006.01) |
| ***A61P 13/12*** | (2006.01) |

(52) U.S. Cl.
CPC ................ *C07K 16/22* (2013.01); *A61P 3/06* (2018.01); *A61P 7/00* (2018.01); *A61P 13/12* (2018.01); *A61K 2039/505* (2013.01); *C07K 2317/24* (2013.01); *C07K 2317/76* (2013.01); *C07K 2317/92* (2013.01)

(58) Field of Classification Search
None
See application file for complete search history.

(56) References Cited

U.S. PATENT DOCUMENTS

2024/0092884 A1* 3/2024 Xu ............................ A61P 7/00

FOREIGN PATENT DOCUMENTS

| | | | |
|---|---|---|---|
| CN | 103732624 A | 4/2014 | |
| CN | 110938144 A * | 3/2020 | .............. A61P 13/12 |
| CN | 112062844 A | 12/2020 | |

* cited by examiner

*Primary Examiner* — Maher M Haddad
(74) *Attorney, Agent, or Firm* — IPRTOP LLC

(57) ABSTRACT

An anti-ANGPTL3 antibody or an antigen-binding fragment thereof. The present invention provides an anti-ANGPTL3 antibody or an antigen-binding fragment thereof, wherein a heavy chain variable region includes complementarity determining regions (CDRs), including CDR-H1 having an amino acid sequence as set forth in SEQ ID No. 1, CDR-H2 having an amino acid sequence as set forth in SEQ ID No. 2, and CDR-H3 having an amino acid sequence as set forth in SEQ ID No. 3; and the CDRs of a light chain variable region includes CDR-L1 having an amino acid sequence as set forth in SEQ ID No. 4, CDR-L2 having an amino acid sequence as set forth in SEQ ID No. 5, and CDR-L3 having an amino acid sequence as set forth in SEQ ID No. 6. The antibody or the antigen-binding fragment thereof provided in the present invention can specifically recognize ANGPTL3.

10 Claims, 6 Drawing Sheets

Specification includes a Sequence Listing.

| Ligand | Antibody | Chi² (RU²) | Ka(1/Ms) | kd(1/s) | KD(M) | Rmax(RU) |
|---|---|---|---|---|---|---|
| ANGPTL3 | Anti-ANGPTL3 antibody | 0.414 | 1.67E+04 | 1.42-03 | 8.48E-08 | 31.56 |

SEQUENCE LISTING

<160> NUMBER OF SEQ ID NOS: 25

<210> SEQ ID NO 1
<211> LENGTH: 5
<212> TYPE: PRT
<213> ORGANISM: Artificial Sequence
<220> FEATURE:
<223> OTHER INFORMATION: CDR-H1

<400> SEQUENCE: 1

Thr Tyr Gly Val Ser
1               5

<210> SEQ ID NO 2
<211> LENGTH: 16
<212> TYPE: PRT
<213> ORGANISM: Artificial Sequence
<220> FEATURE:
<223> OTHER INFORMATION: CDR-H2

<400> SEQUENCE: 2

Val Ile Trp Gly Asp Gly Asn Thr Asn Tyr His Ser Ala Leu Ile Ser
1 5 10 15

<210> SEQ ID NO 3
<211> LENGTH: 12
<212> TYPE: PRT
<213> ORGANISM: Artificial Sequence
<220> FEATURE:
<223> OTHER INFORMATION: CDR-H3

<400> SEQUENCE: 3

Gly Gly Pro Tyr Gly Asn Tyr Val Pro Phe Asp Tyr
1 5 10

<210> SEQ ID NO 4
<211> LENGTH: 15
<212> TYPE: PRT
<213> ORGANISM: Artificial Sequence
<220> FEATURE:
<223> OTHER INFORMATION: CDR-L1

<400> SEQUENCE: 4

Arg Ala Ser Glu Ser Val Asp Ser Tyr Gly Asn Ser Phe Met His
1 5 10 15

<210> SEQ ID NO 5
<211> LENGTH: 7
<212> TYPE: PRT
<213> ORGANISM: Artificial Sequence
<220> FEATURE:
<223> OTHER INFORMATION: CDR-L2

<400> SEQUENCE: 5

Arg Ala Ser Asn Leu Glu Ser
1 5

<210> SEQ ID NO 6
<211> LENGTH: 9
<212> TYPE: PRT
<213> ORGANISM: Artificial Sequence
<220> FEATURE:
<223> OTHER INFORMATION: CDR-L3

<400> SEQUENCE: 6

Gln Gln Ser Asp Glu Glu Pro Pro Thr
1 5

<210> SEQ ID NO 7
<211> LENGTH: 30
<212> TYPE: PRT
<213> ORGANISM: Artificial Sequence
<220> FEATURE:
<223> OTHER INFORMATION: FR-H1

<400> SEQUENCE: 7

Gln Val Gln Leu Lys Glu Ser Gly Pro Gly Leu Val Ala Pro Ser Gln
1 5 10 15

Ser Leu Ser Ile Thr Cys Thr Val Ser Gly Phe Ser Leu Thr
20 25 30

<210> SEQ ID NO 8
<211> LENGTH: 14
<212> TYPE: PRT
<213> ORGANISM: Artificial Sequence
<220> FEATURE:
<223> OTHER INFORMATION: FR-H2

<400> SEQUENCE: 8

Trp Val Arg Gln Pro Pro Gly Lys Gly Leu Glu Trp Leu Gly
1               5                   10

<210> SEQ ID NO 9
<211> LENGTH: 32
<212> TYPE: PRT
<213> ORGANISM: Artificial Sequence
<220> FEATURE:
<223> OTHER INFORMATION: FR-H3

<400> SEQUENCE: 9

Arg Leu Ser Ile Ser Lys Asp Asn Ser Lys Ser Gln Val Phe Leu Lys
1               5                   10                  15

Leu Asn Ser Leu Gln Thr Asp Asp Thr Ala Thr Tyr Tyr Cys Ala Lys
            20                  25                  30

<210> SEQ ID NO 10
<211> LENGTH: 11
<212> TYPE: PRT
<213> ORGANISM: Artificial Sequence
<220> FEATURE:
<223> OTHER INFORMATION: FR-H4

<400> SEQUENCE: 10

Trp Gly Gln Gly Thr Thr Leu Thr Val Ser Ser
1               5                   10

<210> SEQ ID NO 11
<211> LENGTH: 23
<212> TYPE: PRT
<213> ORGANISM: Artificial Sequence
<220> FEATURE:
<223> OTHER INFORMATION: FR-L1

<400> SEQUENCE: 11

Asp Ile Val Leu Thr Gln Ser Pro Ala Ser Leu Ala Val Ser Leu Gly
1               5                   10                  15

Gln Arg Ala Thr Ile Ser Cys
            20

<210> SEQ ID NO 12
<211> LENGTH: 15
<212> TYPE: PRT
<213> ORGANISM: Artificial Sequence
<220> FEATURE:
<223> OTHER INFORMATION: FR-L2

<400> SEQUENCE: 12

Trp Tyr Gln Gln Lys Pro Gly Gln Pro Pro Lys Leu Leu Ile Tyr
1               5                   10                  15

<210> SEQ ID NO 13
<211> LENGTH: 32
<212> TYPE: PRT
<213> ORGANISM: Artificial Sequence
<220> FEATURE:
<223> OTHER INFORMATION: FR-L3

<400> SEQUENCE: 13

Gly Ile Pro Ala Arg Phe Ser Gly Ser Gly Ser Arg Thr Asp Phe Thr
1               5                   10                  15

Leu Thr Ile Asn Pro Val Glu Ala Asp Asp Val Ala Thr Tyr Tyr Cys
            20                  25                  30

<210> SEQ ID NO 14
<211> LENGTH: 10
<212> TYPE: PRT
<213> ORGANISM: Artificial Sequence
<220> FEATURE:
<223> OTHER INFORMATION: FR-L4

<400> SEQUENCE: 14

```
Phe Gly Gly Gly Thr Asn Leu Glu Ile Lys
1               5                   10
```

<210> SEQ ID NO 15
<211> LENGTH: 120
<212> TYPE: PRT
<213> ORGANISM: Artificial Sequence
<220> FEATURE:
<223> OTHER INFORMATION: heavy chain variable region

<400> SEQUENCE: 15

```
Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Thr Tyr
            20                  25                  30

Gly Val Ser Trp Val Arg Gln Pro Pro Gly Lys Gly Leu Glu Trp Leu
        35                  40                  45

Gly Val Ile Trp Gly Asp Gly Asn Thr Asn Tyr His Ser Ala Leu Ile
    50                  55                  60

Ser Arg Leu Ser Ile Ser Lys Asp Asn Ser Lys Ser Gln Val Phe Leu
65                  70                  75                  80

Lys Leu Asn Ser Leu Gln Thr Asp Asp Thr Ala Thr Tyr Tyr Cys Ala
                85                  90                  95

Lys Gly Gly Pro Tyr Gly Asn Tyr Val Pro Phe Asp Tyr Trp Gly Gln
            100                 105                 110

Gly Thr Thr Leu Thr Val Ser Ser
        115                 120
```

<210> SEQ ID NO 16
<211> LENGTH: 111
<212> TYPE: PRT
<213> ORGANISM: Artificial Sequence
<220> FEATURE:
<223> OTHER INFORMATION: light chain variable region

<400> SEQUENCE: 16

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Asn Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Asp
                85                  90                  95

Glu Glu Pro Pro Thr Phe Gly Gly Gly Thr Asn Leu Glu Ile Lys
            100                 105                 110
```

-continued

<210> SEQ ID NO 17
<211> LENGTH: 463
<212> TYPE: PRT
<213> ORGANISM: Artificial Sequence
<220> FEATURE:
<223> OTHER INFORMATION: heavy chain

<400> SEQUENCE: 17

```
Met Ala Val Leu Ala Leu Leu Leu Cys Leu Val Thr Phe Pro Ser Cys
1               5                   10                  15

Val Leu Ser Gln Val Gln Leu Lys Glu Ser Gly Pro Gly Leu Val Ala
            20                  25                  30

Pro Ser Gln Ser Leu Ser Ile Thr Cys Thr Val Ser Gly Phe Ser Leu
        35                  40                  45

Thr Thr Tyr Gly Val Ser Trp Val Arg Gln Pro Pro Gly Lys Gly Leu
    50                  55                  60

Glu Trp Leu Gly Val Ile Trp Gly Asp Gly Asn Thr Asn Tyr His Ser
65                  70                  75                  80

Ala Leu Ile Ser Arg Leu Ser Ile Ser Lys Asp Asn Ser Lys Ser Gln
                85                  90                  95

Val Phe Leu Lys Leu Asn Ser Leu Gln Thr Asp Asp Thr Ala Thr Tyr
            100                 105                 110

Tyr Cys Ala Lys Gly Gly Pro Tyr Gly Asn Tyr Val Pro Phe Asp Tyr
        115                 120                 125

Trp Gly Gln Gly Thr Thr Leu Thr Val Ser Ser Ala Lys Thr Thr Pro
    130                 135                 140

Pro Ser Val Tyr Pro Leu Ala Pro Gly Ser Ala Ala Gln Thr Asn Ser
145                 150                 155                 160

Met Val Thr Leu Gly Cys Leu Val Lys Gly Tyr Phe Pro Glu Pro Val
                165                 170                 175

Thr Val Thr Trp Asn Ser Gly Ser Leu Ser Ser Gly Val His Thr Phe
            180                 185                 190

Pro Ala Val Leu Gln Ser Asp Leu Tyr Thr Leu Ser Ser Ser Val Thr
        195                 200                 205

Val Pro Ser Ser Thr Trp Pro Ser Glu Thr Val Thr Cys Asn Val Ala
    210                 215                 220

His Pro Ala Ser Ser Thr Lys Val Asp Lys Lys Ile Val Pro Arg Asp
225                 230                 235                 240

Cys Gly Cys Lys Pro Cys Ile Cys Thr Val Pro Glu Val Ser Ser Val
                245                 250                 255

Phe Ile Phe Pro Pro Lys Pro Lys Asp Val Leu Thr Ile Thr Leu Thr
            260                 265                 270

Pro Lys Val Thr Cys Val Val Val Asp Ile Ser Lys Asp Asp Pro Glu
        275                 280                 285

Val Gln Phe Ser Trp Phe Val Asp Asp Val Glu Val His Thr Ala Gln
    290                 295                 300

Thr Gln Pro Arg Glu Glu Gln Phe Asn Ser Thr Phe Arg Ser Val Ser
305                 310                 315                 320

Glu Leu Pro Ile Met His Gln Asp Trp Leu Asn Gly Lys Glu Phe Lys
                325                 330                 335

Cys Arg Val Asn Ser Ala Ala Phe Pro Ala Pro Ile Glu Lys Thr Ile
            340                 345                 350

Ser Lys Thr Lys Gly Arg Pro Lys Ala Pro Gln Val Tyr Thr Ile Pro
        355                 360                 365
```

-continued

Pro Pro Lys Glu Gln Met Ala Lys Asp Lys Val Ser Leu Thr Cys Met
    370                 375                 380

Ile Thr Asp Phe Phe Pro Glu Asp Ile Thr Val Glu Trp Gln Trp Asn
385                 390                 395                 400

Gly Gln Pro Ala Glu Asn Tyr Lys Asn Thr Gln Pro Ile Met Asp Thr
                405                 410                 415

Asp Gly Ser Tyr Phe Val Tyr Ser Lys Leu Asn Val Gln Lys Ser Asn
            420                 425                 430

Trp Glu Ala Gly Asn Thr Phe Thr Cys Ser Val Leu His Glu Gly Leu
        435                 440                 445

His Asn His His Thr Glu Lys Ser Leu Ser His Ser Pro Gly Lys
    450                 455                 460

<210> SEQ ID NO 18
<211> LENGTH: 238
<212> TYPE: PRT
<213> ORGANISM: Artificial Sequence
<220> FEATURE:
<223> OTHER INFORMATION: light chain

<400> SEQUENCE: 18

Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Ser Leu Ala
            20                  25                  30

Val Ser Leu Gly Gln Arg Ala Thr Ile Ser Cys Arg Ala Ser Glu Ser
        35                  40                  45

Val Asp Ser Tyr Gly Asn Ser Phe Met His Trp Tyr Gln Gln Lys Pro
    50                  55                  60

Gly Gln Pro Pro Lys Leu Leu Ile Tyr Arg Ala Ser Asn Leu Glu Ser
65                  70                  75                  80

Gly Ile Pro Ala Arg Phe Ser Gly Ser Gly Ser Arg Thr Asp Phe Thr
                85                  90                  95

Leu Thr Ile Asn Pro Val Glu Ala Asp Asp Val Ala Thr Tyr Tyr Cys
            100                 105                 110

Gln Gln Ser Asp Glu Glu Pro Pro Thr Phe Gly Gly Gly Thr Asn Leu
        115                 120                 125

Glu Ile Lys Arg Ala Asp Ala Ala Pro Thr Val Ser Ile Phe Pro Pro
    130                 135                 140

Ser Ser Glu Gln Leu Thr Ser Gly Gly Ala Ser Val Val Cys Phe Leu
145                 150                 155                 160

Asn Asn Phe Tyr Pro Lys Asp Ile Asn Val Lys Trp Lys Ile Asp Gly
                165                 170                 175

Ser Glu Arg Gln Asn Gly Val Leu Asn Ser Trp Thr Asp Gln Asp Ser
            180                 185                 190

Lys Asp Ser Thr Tyr Ser Met Ser Ser Thr Leu Thr Leu Thr Lys Asp
        195                 200                 205

Glu Tyr Glu Arg His Asn Ser Tyr Thr Cys Glu Ala Thr His Lys Thr
    210                 215                 220

Ser Thr Ser Pro Ile Val Lys Ser Phe Asn Arg Asn Glu Cys
225                 230                 235

<210> SEQ ID NO 19
<211> LENGTH: 491
<212> TYPE: PRT
<213> ORGANISM: Artificial Sequence
<220> FEATURE:

<223> OTHER INFORMATION: human ANGPTL3 protein

<400> SEQUENCE: 19

```
Met Leu Leu Val Asn Gln Ser His Gln Gly Phe Asn Lys Glu His Thr
1               5                   10                  15

Ser Lys Met Val Ser Ala Ile Val Leu Tyr Val Leu Leu Ala Ala Ala
            20                  25                  30

Ala His Ser Ala Phe Ala Arg Ile Asp Gln Asp Asn Ser Ser Phe Asp
        35                  40                  45

Ser Leu Ser Pro Glu Pro Lys Ser Arg Phe Ala Met Leu Asp Asp Val
    50                  55                  60

Lys Ile Leu Ala Asn Gly Leu Leu Gln Leu Gly His Gly Leu Lys Asp
65                  70                  75                  80

Phe Val His Lys Thr Lys Gly Gln Ile Asn Asp Ile Phe Gln Lys Leu
                85                  90                  95

Asn Ile Phe Asp Gln Ser Phe Tyr Asp Leu Ser Leu Gln Thr Ser Glu
            100                 105                 110

Ile Lys Glu Glu Glu Lys Glu Leu Arg Arg Thr Thr Tyr Lys Leu Gln
        115                 120                 125

Val Lys Asn Glu Glu Val Lys Asn Met Ser Leu Glu Leu Asn Ser Lys
    130                 135                 140

Leu Glu Ser Leu Leu Glu Glu Lys Ile Leu Leu Gln Gln Lys Val Lys
145                 150                 155                 160

Tyr Leu Glu Glu Gln Leu Thr Asn Leu Ile Gln Asn Gln Pro Glu Thr
                165                 170                 175

Pro Glu His Pro Glu Val Thr Ser Leu Lys Thr Phe Val Glu Lys Gln
            180                 185                 190

Asp Asn Ser Ile Lys Asp Leu Leu Gln Thr Val Glu Asp Gln Tyr Lys
        195                 200                 205

Gln Leu Asn Gln Gln His Ser Gln Ile Lys Glu Ile Glu Asn Gln Leu
    210                 215                 220

Arg Arg Thr Ser Ile Gln Glu Pro Thr Glu Ile Ser Leu Ser Ser Lys
225                 230                 235                 240

Pro Arg Ala Pro Arg Thr Thr Pro Phe Leu Gln Leu Asn Glu Ile Arg
                245                 250                 255

Asn Val Lys His Asp Gly Ile Pro Ala Glu Cys Thr Thr Ile Tyr Asn
            260                 265                 270

Arg Gly Glu His Thr Ser Gly Met Tyr Ala Ile Arg Pro Ser Asn Ser
        275                 280                 285

Gln Val Phe His Val Tyr Cys Asp Val Ile Ser Gly Ser Pro Trp Thr
    290                 295                 300

Leu Ile Gln His Arg Ile Asp Gly Ser Gln Asn Phe Asn Glu Thr Trp
305                 310                 315                 320

Glu Asn Tyr Lys Tyr Gly Phe Gly Arg Leu Asp Gly Glu Phe Trp Leu
                325                 330                 335

Gly Leu Glu Lys Ile Tyr Ser Ile Val Lys Gln Ser Asn Tyr Val Leu
            340                 345                 350

Arg Ile Glu Leu Glu Asp Trp Lys Asp Asn Lys His Tyr Ile Glu Tyr
        355                 360                 365

Ser Phe Tyr Leu Gly Asn His Glu Thr Asn Tyr Thr Leu His Leu Val
    370                 375                 380

Ala Ile Thr Gly Asn Val Pro Asn Ala Ile Pro Glu Asn Lys Asp Leu
385                 390                 395                 400
```

-continued

```
Val Phe Ser Thr Trp Asp His Lys Ala Lys Gly His Phe Asn Cys Pro
                405                 410                 415

Glu Gly Tyr Ser Gly Gly Trp Trp Trp His Asp Glu Cys Gly Glu Asn
            420                 425                 430

Asn Leu Asn Gly Lys Tyr Asn Lys Pro Arg Ala Lys Ser Lys Pro Glu
        435                 440                 445

Arg Arg Arg Gly Leu Ser Trp Lys Ser Gln Asn Gly Arg Leu Tyr Ser
    450                 455                 460

Ile Lys Ser Thr Lys Met Leu Ile His Pro Thr Asp Ser Glu Ser Phe
465                 470                 475                 480

Glu His His His His His His His His His His
                485                 490


<210> SEQ ID NO 20
<211> LENGTH: 1392
<212> TYPE: DNA
<213> ORGANISM: Artificial Sequence
<220> FEATURE:
<223> OTHER INFORMATION: heavy chain coding sequence

<400> SEQUENCE: 20

atggctgtcc tggcactgct cctctgcctg gtgacattcc caagctgtgt cctgtcccag      60

gtgcagctga aggagtcagg acctggcctg gtggcgccct cacagagcct gtccatcaca     120

tgcactgtct cagggttctc attaaccacc tatggtgtaa gctgggttcg ccagcctcca     180

ggaaagggtc tggagtggct gggagtaata tggggtgacg ggaacacaaa ttatcattca     240

gctctcatat ccagactgag catcagcaag gataactcca agagccaagt tttcttaaaa     300

ctgaacagtc tgcaaactga tgacacagcc acgtactact gtgccaaagg aggaccctat     360

ggtaactacg tgccctttga ctactggggc caaggcacca ctctcacagt ctcctcagcc     420

aaaacgacac ccccatctgt ctatccactg gcccctggat ctgctgccca aactaactcc     480

atggtgaccc tgggatgcct ggtcaagggc tatttccctg agccagtgac agtgacctgg     540

aactctggat ccctgtccag cggtgtgcac accttcccag ctgtcctgca gtctgacctc     600

tacactctga gcagctcagt gactgtcccc tccagcacct ggcccagcga gaccgtcacc     660

tgcaacgttg cccacccggc cagcagcacc aaggtggaca agaaaattgt gcccagggat     720

tgtggttgta agccttgcat atgtacagtc ccagaagtat catctgtctt catcttcccc     780

ccaaagccca aggatgtgct caccattact ctgactccta aggtcacgtg tgttgtggta     840

gacatcagca aggatgatcc cgaggtccag ttcagctggt ttgtagatga tgtggaggtg     900

cacacagctc agacgcaacc ccgggaggag cagttcaaca gcactttccg ctcagtcagt     960

gaacttccca tcatgcacca ggactggctc aatggcaagg agttcaaatg cagggtcaac    1020

agtgcagctt tccctgcccc catcgagaaa accatctcca aaaccaaagg cagaccgaag    1080

gctccacagg tgtacaccat tccacctccc aaggagcaga tggccaagga taaagtcagt    1140

ctgacctgca tgataacaga cttcttccct gaagacatta ctgtggagtg gcagtggaat    1200

gggcagccag cggagaacta caagaacact cagcccatca tggacacaga tggctcttac    1260

ttcgtctaca gcaagctcaa tgtgcagaag agcaactggg aggcaggaaa tactttcacc    1320

tgctctgtgt tacatgaggg cctgcacaac caccatactg agaagagcct ctcccactct    1380

cctggtaaat ga                                                        1392


<210> SEQ ID NO 21
<211> LENGTH: 717
```

<212> TYPE: DNA
<213> ORGANISM: Artificial Sequence
<220> FEATURE:
<223> OTHER INFORMATION: light chain coding sequence

<400> SEQUENCE: 21

```
atggagacag acacactcct gctatgggtg ctgctgctct gggttccagg ttccacaggt     60

gacattgtgc tgacccaatc tccagcttct ttggctgtgt ctctagggca gagggccacc    120

atatcctgca gagccagtga aagtgttgat agttatggca atagttttat gcactggtac    180

cagcagaaac caggacagcc acccaaactc ctcatctatc gtgcatccaa cctagaatct    240

gggatccctg ccaggttcag tggcagtggg tctaggacag acttcaccct caccattaat    300

cctgtggagg ctgatgatgt tgcaacctat tactgtcagc agagtgatga ggagcctccg    360

acgttcggtg gaggcaccaa cctggaaatc aaacgggctg atgctgcacc aactgtatcc    420

atcttcccac catccagtga gcagttaaca tctggaggtg cctcagtcgt gtgcttcttg    480

aacaacttct accccaaaga catcaatgtc aagtggaaga ttgatggcag tgaacgacaa    540

aatggcgtcc tgaacagttg gactgatcag gacagcaaag acagcaccta cagcatgagc    600

agcaccctca cgttgaccaa ggacgagtat gaacgacata acagctatac ctgtgaggcc    660

actcacaaga catcaacttc acccattgtc aagagcttca acaggaatga gtgttag       717
```

<210> SEQ ID NO 22
<211> LENGTH: 2756
<212> TYPE: DNA
<213> ORGANISM: Artificial Sequence
<220> FEATURE:
<223> OTHER INFORMATION: synthesized DNA sequence

<400> SEQUENCE: 22

```
gaattcgccg ccaccatggg cgtgatcaag cccgacatga agatcaagct gaggatggag     60

ggcgcagtga acggacacaa gttcgtgatc gagggcgacg gaaagggcaa gcctttcgag    120

ggcaagcaga ccatggacct gacagtgatc gagggagctc ctctgccttt cgcctacgac    180

atcctgacca ccgtgttcga ctacggcaac cgcgtgttcg ccaagtaccc caaggacatc    240

cccgactact tcaagcagac cttccccgag ggctacagtt gggaacggag catgacctac    300

gaggaccagg gcatttgcat cgccaccaac gacatcacca tgatgaaggg cgtcgacgac    360

tgcttcgtgt acaagatccg cttcgacggc gtgaactttc ccgctaacgg ccccgtgatg    420

cagagaaaga ccctcaagtg ggagcccagc accgagaaga tgtacgtcag agacggagtg    480

ctgaagggag acgtgaacat ggccctgctg ctggaaggag gaggacacta ccgctgcgac    540

ttcaagacca cctacaaggc caagaaggtg gtgcagctgc ccgattacca cttcgtggac    600

caccggatcg agatcgtgtc ccacgacaag gactacaaca aggtcaagct gtacgagcac    660

gccgaggctc atagcggact gcctagacag gcaggaggag gaggatctat ggccagcgcc    720

agcggaagcg ataacggatc agcaggagga ctgagacctt ggccaggacc aggagcagca    780

ggactggacg cagatgcagg aggagcagga ggagacgcag cagcttcagt ggccgccgct    840

ctgcagtcta gaagaagagc agccggcgag acctacagca gaaaggagaa gtctctgggc    900

ctcctctgcg agaacttcgt gaacctgtac ggccagaccg gctcagatgg agcaggagca    960

gcagcagacg cagacggaca gcctagcgat atttgcctgg acgccgcagc tctgagactg   1020

cacgtgccta gaaggcggat ctacgacatc gtgaacgtgc tggaggctct gggagtggtc   1080

gtgagaaagg ccaagaaccg gtacacttgg accggaacag cccacctggc tacaacactg   1140
```

gccgctctgg ctacagcagc agcaagagga gacgcagacg acgatggaga actgatggac 1200
ggagcaggag acggaggagg atctagcgac gacggagaag gaggagcctc tcagacacca 1260
gcagctccag gaacagcagc agcagctctg gcagctgtgg tgacagtgta caggctgagg 1320
aagagcgtgg acaccaggaa ggagaagagc ctgggagtgc tgagccagag attcgtgcag 1380
ctcttcctgc tgggcggaac agagatgcct cctggagacg tgggaacaac atctagcgcc 1440
gcagcaggag ctccaggatc tggacctagc ggaggaggag gagtgggaga tagcagcgtg 1500
ggcgatacag caggaatcgt ggctccagga gccccaggca atagatctag cacaggcctg 1560
gcagacggag gatctggagg agtggctaac ggagcagacg gaccaggagg atctatcgtg 1620
tctctggaag ccgccgcagc tagactgctg ggaccttctg tgggagctac accagcagca 1680
gtggccgcca aaatgaagac caaggtccgc cggctgtacg acatcgccaa catcctggcc 1740
agcctgaaca tcatcaagaa ggtgcacacc gccagcagga aacccgcttt tcgctggctg 1800
ggaccagcta cacctcaggc tccagctaca gccggaagaa gcacagcagg agcagctctg 1860
acagtgccag gagctaacgg caagcctccc ctgagacaca gaaggcctag acctctgctg 1920
agactgctgc cagctccagg cgacagaacc cccacttgca gaagactggg cagaagcgga 1980
agaggcagcg gatttggctg cagacccact tgccagtgta gagcagatcc tcctagactg 2040
ctggctcagc aggtcagacc tagcagacca ggaacccaca ccgctagcac caagggacct 2100
agcgtgttcc ctctggctcc ttgtagcaga agcaccagcg agtctacagc agctctgggt 2160
tgcctggtga aggactactt ccccgagcca gtgaccgtgt cttggaacag cggagctctg 2220
accagcggag tgcacacatt cccagcagtg ctgcagagca gcggactgta ctctctgagc 2280
agcgtggtga ccgtgccttc ttctagcctg ggcaccaaga cctacacttg caacgtggac 2340
cacaagccca gcaacaccaa ggtggacaag cgggtggaga gcaaatacgg ccctccttgc 2400
cctccttgcc ctgctccaga gtttctggga ggacctagcg tgttcctgtt ccctcccaag 2460
cccaaggaca ccctgatgat cagcaggacc cccgaagtga cttgcgtggt ggtggacgtg 2520
tctcaggagg accccgaggt gcagttcaat tggtacgtgg acggagtgga ggtgcacaac 2580
gctaagacca agcccaggga ggagcagttc aacagcacct acagggtggt gtccgtgctg 2640
acagtggtgc accaggattg gctgaacggc aaggagtaca agtgcaaggt gtccaacaag 2700
ggcctgccca gcagcatcga gaagaccatc agcaaggcca agggccagcc tagaga 2756

<210> SEQ ID NO 23
<211> LENGTH: 267
<212> TYPE: DNA
<213> ORGANISM: Artificial Sequence
<220> FEATURE:
<223> OTHER INFORMATION: synthesized DNA sequence added at the 3' end

<400> SEQUENCE: 23
gctagcgtgg tgtgcctcct gaacaacttc taccccaggg aggccaaggt ccagtggaag 60
gtggacaacg ctctgcagag cggcaactct caggagagcg tgacagagca ggacagcaag 120
gacagcacct acagcctgag cagcacactg accctgtcta aggccgacta cgagaagcac 180
aaggtgtacg cttgcgaggt gacccatcag ggactgtcta gcccagtgac caagagcttc 240
aaccgaggcg agtgctaatg aggatcc 267

<210> SEQ ID NO 24
<211> LENGTH: 57
<212> TYPE: DNA
<213> ORGANISM: Artificial Sequence -continued

```
<220> FEATURE:
<223> OTHER INFORMATION: the sequence added to the N-terminus of SEQ ID
      No. 20

<400> SEQUENCE: 24

atgggctgga gctgcatcat cctgttcctg gtggccaccg ccaccggcgt gcacagc       57


<210> SEQ ID NO 25
<211> LENGTH: 57
<212> TYPE: DNA
<213> ORGANISM: Artificial Sequence
<220> FEATURE:
<223> OTHER INFORMATION: the sequence added to the C-terminus of SEQ ID
      No. 21

<400> SEQUENCE: 25

atgggctgga gctgcatcat cctgttcctg gtggccaccg ccaccggcgt gcacagc       57
```

ANTI-ANGPTL3 ANTIBODY OR ANTIGEN-BINDING FRAGMENT THEREOF, AND PREPARATION METHOD AND USE THEREOF

CROSS REFERENCE TO RELATED PATENT APPLICATION

The present application is the US national stage of PCT/CN2021/084206 filed on 2021 Mar. 30.

FIELD OF TECHNOLOGY

The present invention relates to the field of biotechnologies, and in particular, to an anti-ANGPTL3 antibody or an antigen-binding fragment thereof, and a preparation method and use thereof.

BACKGROUND

Proteinuria is a common clinical manifestation of renal diseases, mainly related to renal podocyte damage. There is currently no specific treatment for causative factors.

Angiopoietin-like protein 3 (ANGPTL3) is a secreted glycoprotein that contains a coiled-coil domain (CCD) and a fibrinogen-like domain (FLD). The CCD can inhibit lipoprotein lipase and regulate lipid metabolism. The FLD is involved in podocyte damage by binding to the receptor integrin αvβ3.

At present, the monoclonal antibody against ANGPTL3 is only used for detection in Western-Blot, ELISA and other detective experiments, and there is no therapeutic antibody against the functional domain of ANGPTL3.

SUMMARY

In view of the foregoing disadvantages in the related art, an object of the present invention is to provide an anti-ANGPTL3 antibody or an antigen-binding fragment thereof, and a preparation method and use thereof, to resolve the problems in the related art.

In order to accomplish the above object and other related objects, according to an aspect, the present invention provides an anti-ANGPTL3 antibody or an antigen-binding fragment thereof, including a heavy chain variable region and a light chain variable region, wherein the heavy chain variable region includes complementarily determining regions (CDRs),which includes CDR-H1 having an amino acid sequence as set forth in SEQ ID No. 1, CDR-H2 having an amino acid sequence as set forth in SEQ ID No. 2, and CDR-H3 having an amino acid sequence as set forth in SEQ ID No. 3; and the light chain variable region includes complementarity determining regions (CDRs), which includes CDR-L1 having an amino acid sequence as set forth in SEQ ID No. 4, CDR-L2 having an amino acid sequence as set forth in SEQ ID No. 5, and CDR-L3 having an amino acid sequence as set forth in SEQ ID No. 6.

According to another aspect, the present invention provides an isolated polynucleotide, encoding the foregoing anti-ANGPTL3 antibody or the antigen-binding fragment thereof.

According to another aspect, the present invention provides a construct, including the foregoing isolated polynucleotide.

According to another aspect, the present invention provides an expression system, including the foregoing construct or including a genome which incorporates the exogenous foregoing polynucleotide.

According to another aspect, the present invention provides a method for preparing the foregoing anti-ANGPTL3 antibody or the antigen-binding fragment thereof, including: culturing the foregoing expression system under proper conditions to express the anti-ANGPTL3 antibody or the antigen-binding fragment thereof, and carrying out isolation and purification to provide the anti-ANGPTL3 antibody or the antigen-binding fragment thereof.

According to another aspect, the present invention provides use of the foregoing anti-ANGPTL3 antibody or the antigen-binding fragment thereof, or a culture of the foregoing expression system in preparing a drug and/or a reagent.

According to another aspect, the present invention provides a drug composition, including the foregoing anti-ANGPTL3 antibody or the antigen-binding fragment thereof, or a culture of the foregoing expression system.

According to another aspect, the present invention provides a kit for detection, including the foregoing anti-ANGPTL3 antibody or the antigen-binding fragment thereof.

DETAILED DESCRIPTION

Figure 1:
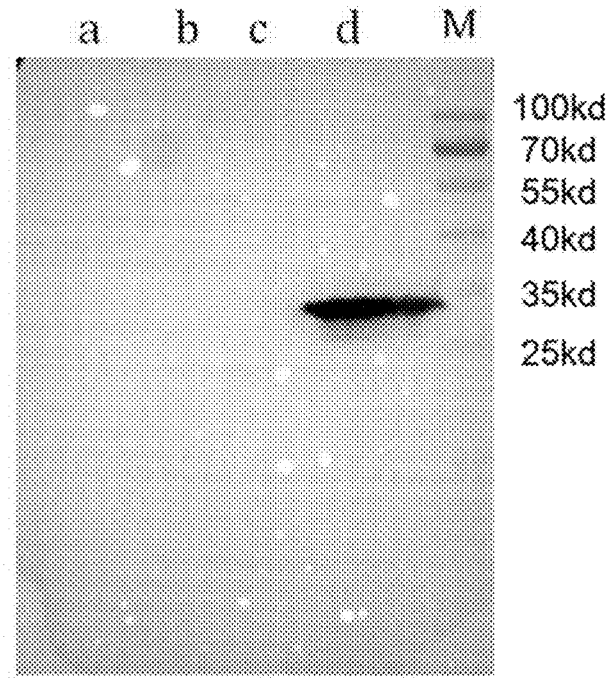
FIG. 1 shows the results of Western-Blot verification of the anti-ANGPTL3 monoclonal antibody in Example 1 of the present invention.

It was unexpectedly discovered by the inventors through a lot of research that an anti-ANGPTL3 antibody or an antigen-binding fragment thereof can specifically recognize ANGPTL3 and antagonize the damage to podocytes caused by ANGPTL3, so that it can be used in the treatment of proteinuria. Based on this, the present invention is completed.

According to a first aspect, the present invention provides an anti-ANGPTL3 antibody or an antigen-binding fragment thereof, which may include a heavy chain variable region and a light chain variable region, wherein the heavy chain variable region includes complementarity determining region (CDR), which may include CDR-H1 having an amino acid sequence as set forth in SEQ ID No. 1, CDR-H2 having an amino acid sequence as set forth in SEQ ID No. 2, and CDR-H3 having an amino acid sequence as set forth in SEQ ID No. 3; and/or the light chain variable region includes complementarity determining region (CDR), which may include CDR-L1 having an amino acid sequence as set forth in SEQ ID No. 4, CDR-L2 having an amino acid sequence as set forth in SEQ ID No. 5, and CDR-L3 having an amino acid sequence as set forth in SEQ ID No. 6. The anti-ANGPTL3 antibody or the antigen-binding fragment thereof is an antibody (442-460aa, 415-430aa) against the FLD domain of ANGPTL3 (NP_055310.1), which can specifically recognize ANGPTL3, and also can block the binding of the FLD (Fibrinogen-like domain) of ANGPTL3 to integrin αVβ3 and antagonize the damage to podocytes caused by ANGPTL3, thereby protecting the podocytes.

The anti-ANGPTL3 antibody or the antigen-binding fragment thereof may generally be a monoclonal antibody. The monoclonal antibody generally refers to a class of antibodies that are substantially identical (except for a few possible naturally occurring mutations). Monoclonal antibodies are generally directed against specific determinants on an antigen.

The anti-ANGPTL3 antibody or the antigen-binding fragment thereof may generally be derived from mouse (*Mus musculus*), for example, may be obtained from murine hybridoma cells, or may have a CDR derived from mouse.

The anti-ANGPTL3 antibody or the antigen-binding fragment thereof may further include an framework region (FR). The CDR may usually be arranged in order with the FR. In an example, the heavy chain variable region of the anti-ANGPTL3 antibody or the antigen-binding fragment thereof may include FR-H1, CDR-H1, FR-H2, CDR-H2, FR-H3, CDR-H3, and FR-H4 in sequence from the N-terminus to the C-terminus, and the light chain variable region of the anti-ANGPTL3 antibody or the antigen-binding fragment thereof may include FR-L1, CDR-L1, FR-L2, CDR-L2, FR-L3, CDR-L3, and FR-L4 in sequence from the N-terminus to the C-terminus. In another example, the FR region of the heavy chain variable region may include FR-H1 having an amino acid sequence as set forth in SEQ ID No. 7, FR-H2 having an amino acid sequence as set forth in SEQ ID No. 8, FR-H3 having an amino acid sequence as set forth in SEQ ID No. 9, and FR-H4 having an amino acid sequence as set forth in SEQ ID No. 10; and the FR region of the light chain variable region may include FR-L1 having an amino acid sequence as set forth in SEQ ID No. 11, FR-L2 having an amino acid sequence as set forth in SEQ ID No. 12, FR-L3 having an amino acid sequence as set forth in SEQ ID No. 13, and FR-L4 having an amino acid sequence as set forth in SEQ ID No. 14.

The anti-ANGPTL3 antibody or the antigen-binding fragment thereof may generally be humanized, for example, its FR may be derived from human (*Homo sapiens*). Humanized antibodies are immunoglobulins including human FRs and one or more CDRs from non-human (such as mouse, rat, or synthetic) immunoglobulins. The non-human immunoglobulin that provides the CDRs is referred to as the "donor", and the human immunoglobulin that provides the FRs is referred to as the "acceptor". In an example, all CDRs may be from a donor immunoglobulin in a humanized immunoglobulin. In another example, there may be no constant region, but if there is, the constant region typically needs to be substantially identical to a constant region of a human immunoglobulin, at least about 85-90% identical, preferably about 95% or more identical. Thus, all parts, except for possible CDRs, of the humanized immunoglobulin are substantially identical to the corresponding parts of the native human immunoglobulin sequence. Humanized or other monoclonal antibodies may have additional conservative amino acid substitutions that have substantially no effect on binding to antigen or other immunoglobulin functions. Humanized antibodies may be constructed by genetic engineering (referring to U.S. Pat. No. 5,585,089).

In a specific embodiment of the present invention, the heavy chain variable region of the anti-ANGPTL3 antibody or the antigen-binding fragment thereof may include: a) a polypeptide fragment having the amino acid sequence as set forth in SEQ ID No. 15; or b) a polypeptide fragment having an amino acid sequence having at least 80% sequence identity with SEQ ID No. 15 and having the same function as the polypeptide fragment in a). Specifically, the polypeptide fragment in b) refers to a polypeptide fragment having an amino acid sequence obtained by substituting, deleting, or adding one or more (specifically 1-50, 1-30, 1-20, 1-10, 1-5, or 1-3) amino acids to the amino acid sequence as set forth in SEQ ID No. 15, or obtained by adding one or more (specifically 1-50, 1-30, 1-20, 1-10, 1-5, or 1-3) amino acids to the N-terminus and/or C-terminus of the amino acid sequence as set forth in SEQ ID No. 15, and having the same function as the polypeptide fragment of SEQ ID No. 15. For example, the function may be the capability of specifically binding to ANGPTL3 or may be the capability of blocking the binding of the FLD of ANGPTL3 to integrin αVβ3, thereby antagonizing the damage to podocytes caused by ANGPTL3, and protecting the podocytes. The amino acid sequence of the anti-ANGPTL3 antibody or the antigen-binding fragment thereof in b) may have more than 80%, 85%, 90%, 93%, 95%, 97%, or 99% sequence identity to SEQ ID No. 15.

As used herein, sequence identity refers to the percentage of identical residues in the sequences participating in the alignment. Sequence identity of two or more sequences of interest may be calculated using computational software, available from NCBI, well known in the art.

In another specific embodiment of the present invention, the light chain variable region of the anti-ANGPTL3 antibody or the antigen-binding fragment thereof may include: c) a polypeptide fragment having the amino acid sequence as set forth in SEQ ID No. 16; or d) a polypeptide fragment having an amino acid sequence having at least 80% sequence identity with SEQ ID No. 16 and having the same function as the polypeptide fragment in a). Specifically, the polypeptide fragment in d) refers to a polypeptide fragment having an amino acid sequence obtained by substituting, deleting, or adding one or more (specifically 1-50, 1-30, 1-20, 1-10, 1-5, or 1-3) amino acids to the amino acid sequence as set forth in SEQ ID No. 16, or obtained by adding one or more (specifically 1-50, 1-30, 1-20, 1-10, 1-5, or 1-3) amino acids to the N-terminus and/or C-terminus of the amino acid sequence as set forth in SEQ ID No. 16, and having the same function as the polypeptide fragment of SEQ ID No. 16. For example, the function may be the capability of specifically binding to ANGPTL3 or may be the capability of blocking the binding of the FLD of ANGPTL3 to integrin αVβ3, thereby antabonizing the damage to podocytes caused by ANGPTL3, and protecting the podocytes. The amino acid sequence of the anti-ANGPTL3 antibody or the antigen-binding fragment thereof in d) may have more than 80%, 85%, 90%, 93%, 95%, 97%, or 99% sequence identity to SEQ ID No. 16.

In another specific embodiment of the present invention, the amino acid sequence of the heavy chain of the anti-ANGPTL3 antibody or the antigen-binding fragment thereof may include the amino acid sequence as set forth in SEQ ID No. 17.

In another specific embodiment of the present invention, the amino acid sequence of the light chain of the anti-ANGPTL3 antibody or the antigen-binding fragment thereof may include the amino acid sequence as set forth in SEQ ID No. 18.

The anti-ANGPTL3 antibody or the antigen-binding fragment thereof may be a Fab fragment, a Fab' fragment, a $F(ab')_2$ fragment, a bispecific Fab dimer (Fab2), a trispecific Fab trimer (Fab3), Fv, a single-chain Fv protein ("scFv"), bis-scFv, $(scFv)_2$, a minibody, a diabody, a tribody, a tetrabody, a disulfide-stabilized Fv protein ("dsFv"), or a single-domain antibody (sdAb, nanobody), and other various parts that can be responsible for binding to antigen in full-length antibodies.

According to a second aspect, the present invention provides an isolated polynucleotide, encoding the anti-ANGPTL3 antibody or the antigen-binding fragment thereof provided in the present invention according to the first aspect. The polynucleotide may be RNA, DNA, cDNA, or the like. A method for providing the isolated polynucleotide should be known to those skilled in the art. For example, the isolated polynucleotide may be prepared by automated DNA synthesis and/or recombinant DNA technique, or may be isolated from proper natural sources.

According to a third aspect, the present invention provides a construct, including the isolated polynucleotide provided in the present invention according to the second aspect. A proper method for constructing the construct should be known to those skilled in the art. For example, the construct may be constructed by in vitro recombinant DNA technique, DNA synthesis technique, in vivo recombinant technique, or the like. More specifically, it may be constructed by inserting the foregoing isolated polynucleotide into the multiple cloning site of an expression vector. In the present invention, the expression vector generally refers to various commercially available expression vectors well known in the art, such as bacterial plasmids, bacteriophages, yeast plasmids, plant cell viruses, mammalian cell viruses such as adenovirus, retrovirus, or other vectors. Generally, a proper vector may include an origin of replication, a promoter sequence, convenient restriction enzyme sites, and one or more selectable markers that are functional in at least one organism. For example, these promoters may include, but are not limited to, the lac or trp promoter of *E. coli*; the λ phage PL promoter; and the eukaryotic promoter including the CMV immediate early promoter, the HSV thymidine kinase promoter, the early and late SV40 promoters, the methanol oxidase promoter of *Pichia pastoris*, and other known promoters that can control gene expression in prokaryotic or eukaryotic cells or in viruses. Marker genes may be used to provide phenotypic traits for selection of transformed host cells, for example, may be comprising, but not limited to, dihydrofolate reductase, neomycin resistance, and green fluorescent protein (GFP) for eukaryotic cell culture, or tetracycline or ampicillin resistance for *E. coli*. When the polynucleotide is expressed, the expression vector may also include an enhancer sequence. The insertion of the enhancer sequence into the vector will enhance transcription. The enhancer is a cis-acting factor of DNA usually with about 10-300 base pairs, acting on a promoter to enhance the transcription of gene.

According to a fourth aspect, the present invention provides an expression system, including the construct provided in the present invention according to the third aspect, or including a genome which incorporates the exogenous polynucleotide provided in the present invention according to the second aspect, to express the foregoing anti-ANGPTL3 antibody or the antigen-binding fragment thereof. The expression system may be host cells, and any cells suitable for the expression vector to express may be used as the host cells. For example, the host cells may be prokaryotic cells, such as bacterial cells; or lower eukaryotic cells, such as yeast cells and filamentous fungal cells; or higher eukaryotic cells, such as mammalian cells. Representative examples of the host cells include: *Escherichia coli, Streptomyces*; bacterial cells of *Salmonella typhimurium*; fungal cells such as yeast cells, filamentous fungal cells, and plant cells; *Drosophila* S2 or Sf9 cells; and CHO cells, COS cells, 293 cells, or Bowes animal melanoma cells. A method for introducing the construct into host cells should be known to those skilled in the art, including microinjection, biolistics, electroporation, virus-mediated transformation, electron bombardment, calcium phosphate precipitation, and the like.

According to a fifth aspect, the present invention provides a method for preparing the anti-ANGPTL3 antibody or the antigen-binding fragment thereof provided in the present invention according to the first aspect. Those skilled in the art may select a proper method to prepare the anti-ANGPTL3 antibody or the antigen-binding fragment thereof. For example, the preparation method may include: culturing the expression system provided in the present invention according to the fourth aspect under proper conditions, to express the anti-ANGPTL3 antibody or the antigen-binding fragment thereof, collecting a culture containing the anti-ANGPTL3 antibody or the antigen-binding fragment thereof, and carrying out isolation and purification to provide the anti-ANGPTL3 antibody or the antigen-binding fragment thereof.

According to a sixth aspect, the present invention provides use of the anti-ANGPTL3 antibody or the antigen-binding fragment thereof provided in the present invention according to the first aspect or a culture of the expression system provided in the present invention according to the fourth aspect in preparing a drug and/or a reagent. As described above, the anti-ANGPTL3 antibody or the antigen-binding fragment thereof provided in the present invention is an antibody against the FLD of ANGPTL3, can specifically recognize ANGPTL3, so that it can be used to prepare a detection reagent. In addition, the anti-ANGPTL3 antibody or the antigen-binding fragment thereof can also block the binding of the FLD of ANGPTL3 to integrin αVβ3, so that it can be used to prepare an ANGPTL3 blocker (for example, a blocker against the FLD of ANGPTL3), more specifically, a blocker against the binding of ANGPTL3 to integrin αVβ3, or can be used to prepare an integrin αVβ3 antagonist, more specifically, an antagonist against the binding of integrin αVβ3 to ANGPTL3. The anti-ANGPTL3 antibody or the antigen-binding fragment thereof can inhibit the related functions of ANGPTL3 by blocking against the FLD of ANGPTL3, so that it can be used in the treatment of related diseases mediated by ANGPTL3 (for example, the FLD of ANGPTL3) and/or integrin αvβ3, specifically kidney diseases, diseases related to podocyte damage, proteinuria, hypoalbuminemia, hypercholesterolemia, or the like. These diseases are usually associated with kidney damage.

According to a seventh aspect, the present invention provides a drug composition, including the anti-ANGPTL3 antibody or the antigen-binding fragment thereof provided in the present invention according to the first aspect or a culture of the expression system provided in the present invention according to the fourth aspect. In the drug composition, the anti-ANGPTL3 antibody or the antigen-binding fragment thereof or the culture usually has a therapeutically effective dose. In the present invention, "therapeutically effective dose" generally refers to a dose that, after a proper period of administration, can lead to reduction in the severity of disease symptoms. Those skilled in the art may select a proper therapeutically effective dose according to the actual situation, such as the age of the subject, the severity of symptoms of the subject, the selected specific composition, or the route of administration. The prescription (for example, the determination of dosage) of treatment may be determined by a physician with factors considered generally including, but not limited to, the disease being treated, the condition of the patient, the site of delivery, the method of administration, and other factors.

The drug composition may also include a pharmaceutically acceptable carrier. The carrier may include various excipients and diluents. These carriers are not essential active ingredients and are not unduly toxic after administration. Proper carriers should be well known to those skilled in the art. For example, a thorough discussion of pharmaceutically acceptable carriers may be found in Remington's Pharmaceutical Sciences (Mack Pub.Co., N.J., 1991).

According to an eighth aspect, the present invention provides a method for treatment, including: administering to a subject a therapeutically effective dose of the anti-ANGPTL3 antibody or the antigen-binding fragment thereof provided in the present invention according to the first aspect, a culture of the expression system provided in the present invention according to the fourth aspect, or the drug composition provided in the present invention according to the seventh aspect.

In the present invention, the term "treatment" include the prophylactic, curative, or palliative treatment that results in the desired pharmaceutical and/or physiological effect. Preferably, the effect refers to medically reducing one or more symptoms of the disease or completely eliminating the disease, or retarding or delaying the disease and/or reducing the risk of developing or worsening the disease.

In the present invention, the "subject" generally includes humans, non-human primates, or other mammals (such as dogs, cats, horses, sheep, pigs, or cows), which can benefit from treatment with the formulation, kit, or co-formulation.

In the present invention, the anti-ANGPTL3 antibody or the antigen-binding fragment thereof, the culture of the expression system, or the drug composition may be used as a single active ingredient, or may be used in combination with other agents, so as to be administered in combination therapy. For example, the anti-ANGPTL3 antibody or the antigen-binding fragment thereof, the culture of the expression system, or the drug composition may be used in combination with at least one drug for the treatment of proteinuria.

According to a ninth aspect, the present invention provides a kit for detection, including the anti-ANGPTL3 antibody or the antigen-binding fragment thereof provided in the present invention according to the first aspect. As described above, the anti-ANGPTL3 antibody or the antigen-binding fragment thereof is an antibody against the FLD of ANGPTL3, can specifically recognize ANGPTL3, so that it can be used to prepare a detection reagent. The kit may also include, as required, a container, a control (negative or positive), a buffer, an auxiliary agent, and the like, which may be selected by those skilled in the art according to specific conditions.

According to a tenth aspect, the present invention provides a method for detection of ANGPTL3. The method for detection may include: obtaining a sample (for example, a cell and/or tissue sample); dissolving the sample in a medium; and detecting a level of ANGPTL3 in the dissolved sample through the anti-ANGPTL3 antibody or the antigen-binding fragment thereof provided in the present invention according to the first aspect.

The anti-ANGPTL3 antibody or the antigen-binding fragment thereof provided in the present invention can specifically recognize ANGPTL3, block the binding of the FLD of ANGPTL3 to integrin αVβ3, and antagonize the damage to podocytes caused by ANGPTL3, thereby protecting the podocytes. Therefore, it has a good industrialization prospect.

The following describes implementations of the present invention by using specific examples. A person skilled in the art may easily understand other advantages and effects of the present invention from the content disclosed in this specification. The present invention may also be implemented or applied through other different specific implementations. Various details in this specification may also be modified or changed based on different viewpoints and applications without departing from the spirit of the present invention.

Before further describing the specific implementations of the present invention, it should be understood that the protection scope of the present invention is not limited to the following specific implementations; and it should also be understood that the terms used in the examples of the present invention are for describing specific implementations, rather than for limiting the protection scope of the present invention.

When numerical ranges are given in the examples, it should be understood that, unless otherwise specified in the present invention, both endpoints of each numerical range and any number between the two endpoints may be selected. Unless otherwise defined, all technical and scientific terms used in the present invention have the same meaning as commonly understood by a person skilled in the art. In addition to the specific methods, equipment and materials used in the example, according to the mastery of the related art by a person skilled in the art and the description of the present invention, the present invention may be implemented using any methods, equipment and materials similar or equivalent to those described in the examples of the present invention.

Unless otherwise specified, the experimental methods, detection methods and preparation methods disclosed in the present invention all adopt the conventional molecular biology, biochemistry, chromatin structure and analysis, analytical chemistry, cell culture, recombinant DNA techniques, and conventional techniques in the related art. These techniques are well described in the existing literature, specifically referring to Sambrook et al., MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, Chromatin (P. M. Wassarman and A. P. Wolffe, eds.), Academic Press, San Diego, 1999; and METHODS IN MOLECULAR BIOLOGY, Vol. 119, Chromatin Protocols (P. B. Becker, ed.) Humana Press, Totowa, 1999.

EXAMPLE 1

Screening of Anti-ANGPTL3 Monoclonal Antibody

The human ANGPTL3 protein (with the amino acid sequence as set forth in SEQ ID No. 19) was used as the immunogen. The antigen protein was dissolved in normal saline and uniformly mixed with an equal volume of Freund's adjuvant, and then injected subcutaneously into 10 BALB/c mice at multiple points once a week, for a total of 4 times of immunization. Blood was collected for ELISA detection 7 days after the second immunization. Indirect detection by plate-coated ELISA was carried out with protein and His-independent protein, respectively. Serum was tested after three immunizations. If the protein for titer of serum from the animal meets the fusion requirements (the OD value of the serum at 1:8000 dilution is >1.0) under the detection of ELISA, it was taken for next step.

```
                                         (SEQ ID NO. 19)
MLLVNQSHQGFNKEHTSKMVSAIVLYVLLAAAAHSAFARIDQDNSSFDSL

SPEPKSRFAMLDDVKILANGLLQLGHGLKDFVHKTKGQINDIFQKLNIFD

QSFYDLSLQTSEIKEEEKELRRTTYKLQVKNEEVKNMSLELNSKLESLLE

EKILLQQKVKYLEEQLTNLIQNQPETPEHPEVTSLKTFVEKQDNSIKDLL

QTVEDQYKQLNQQHSQIKEIENQLRRTSIQEPTEISLSSKPRAPRTTPFL

QLNEIRNVKHDGIPAECTTIYNRGEHTSGMYAIRPSNSQVFHVYCDVISG

SPWTLIQHRIDGSQNFNETWENYKYGFGRLDGEFWLGLEKIYSIVKQSNY

VLRIELEDWKDNKHYIEYSFYLGNHETNYTLHLVAITGNVPNAIPENKDL

VFSTWDHKAKGHFNCPEGYSGGWWWHDECGENNLNGKYNKPRAKSKPERR

RGLSWKSQNGRLYSIKSTKMLIHPTDSESFEHHHHHHHHHH**
```

Determining the experimental animals for fusion according to the immunoassay results, the two mice with the best titer were selected for fusion. The fusion efficiency can reach 1 hybridoma cell produced per 2000 B cells. There were 15 96-well plates for each fusion. The plate was coated with protein, and the supernatant of hybridoma cells was screened by indirect ELISA. The detailed detection results are shown in Table 1.

Experimental Steps of the Indirect ELISA:

(1) Dilution with coating solution: ANGPTL3-FLD (i.e., the human ANGPTL3 protein of SEQ ID No. 19) was diluted with a coating solution (a. 50 mM carbonate buffer with pH 9.6: $Na_2CO_3$ 1.59 g, $NaHCO_3$ 2.63 g, and distilled water to 1 L) to 1 μg/mL, and then added into an enzyme-linked plate in 100 μL per well, and then the enzyme-linked plate was placed in a wet box at 4° C. overnight.

(2) The enzyme-linked plate was washed three times, blocked with 0.5% BSA in 200 μL per well, and then placed in the wet box at 37° C. for 1 h.

(3) The supernatant of hybridoma cells obtained in different dilution gradients was added into the enzyme-linked plate with 100 μL per well, and then placed in the wet box at 37° C. to react for 1 h.

(4) The enzyme-linked plate was washed three times, the Biotin-rabbit-anti-mouse polyclonal antibody (Jackson, 315-065-044, 0.2 μg/mL) was added into the enzyme-linked plate, and then placed in the wet box at 37° C. to react for 1 h.

(5) The enzyme-linked plate was washed three times, and then the Peroxidase-Labeled Streptavidin (1:4000) (Beyotime, Nanjing, A0303) was added into the enzyme-linked plate to react at room temperature for 45 min.

(6) The enzyme-linked plate was washed five times, and then 100 μL of TMB chromogenic solution was added into the enzyme-linked plate to react for 3 min, the reaction was stopped with 100 μL of $H_2SO_4$ (1 mol/L), and the reading at 450 nm was taken by an ELISA reader.

TABLE 1

| | OD 450 | | | OD 450 | |
|---|---|---|---|---|---|
| Cell line | A | B | Cell line | A | B |
| 1A12F4 | 2.090 | 0.168 | 20C2B8 | 2.138 | 0.196 |
| 5E5F6 | 2.448 | 0.148 | 22G6E11 | 2.015 | 0.186 |
| 6B1E11 | 2.277 | 0.098 | 25G3A5 | 2.204 | 0.121 |
| 11C10F3 | 1.935 | 0.164 | 28E8D10 | 2.367 | 0.150 |
| 16F12F4 | 1.989 | 0.191 | 30B10D1 | 2.245 | 0.178 |
| PC (Antiserum 1:1000) Species | 2.614 | 0.208 | Negative Control Supernatant BALB/c mouse | 0.195 | 0.112 |

Purification of antibody: After 1 mL or 5 mL affinity chromatography column was equilibrated with 1×TBS buffer for 5 column volumes, the cell culture supernatant according objected with a volume determined according to the protein content in this volume less than the maximum loading into the column. After the injection was completed, the column was rinsed with 1×TBS buffer for 5 column volumes, and then eluted with 100 mM Gly-HCl (pH 3.5) for 4 column volumes. The elution peaks were collected. 1.5 M Tris solution (pH 8.5) was added at 1/10 of the collection volume into the eluted liquid to adjust pH to neutral. The protein concentration was measured by using a micro UV spectrophotometer.

The protein sample was further purified by molecular-sieve chromatography before being used for animal injection, with a packing of Sephadex 200, a column volume of 120 mL (inner diameter 16 mm and height 600 mm), and a sampling amount within 5% of the column volume. The purified sample was equilibrated and eluted with PBS. The eluted liquid was concentrated by using an ultrafiltration tube and then measured the protein concentration, and then stored at −80° C. for use.

Confirmatory screening: The Western-Blot verification was carried out to detect the recombinant protein (ANGPTL3-CCD or ANGPTL3-FLD), the anti-ANGPTL3 monoclonal antibody as the primary antibody (purified from the supernatant of the 5E5F6 cell line culture medium), and the peroxidase-labeled rabbit anti-mouse IgG as the secondary antibody (referring to FIG. 1, a. negative control; b. recombinant protein ANGPTL3-CCD; c. negative control; and d. recombinant protein ANGPTL3-FLD). The experimental results show that the anti-ANGPTL3 monoclonal antibody can specifically bind to ANGPTL3-FLD. (the method for obtaining the mouse recombinant proteins ANGPTL3-CCD and ANGPTL3-FLD, refer to Zerbs S et al., Methods Enzymol, Small-scale expression of proteins in *E. coli*.)

The purified antibody (purified from the supernatant of the 5E5F6 cell line culture medium) was sequenced, and the antibody sequence was analyzed by NCBIIgBLAST.

The full sequence of the heavy chain of the obtained antibody is as follows:

```
                                    (SEQ ID No. 17)
MAVLALLLCLVTFPSCVLSQVQLKESGPGLVAPSQSLSITCTVSGFSLTT
YGVSWVRQPPGKGLEWLGVIWGDGNTNYHSALISRLSISKDNSKSQVFLK
LNSLQTDDTATYYCAKGGPYGNYVPFDYWGQGTTLTVSSAKTTPPSVYPL
APGSAAQTNSMVTLGCLVKGYFPEPVTVTWNSGSLSSGVHTFPAVLQSDL
YTLSSSVTVPSSTWPSETVTCNVAHPASSTKVDKKIVPRDCGCKPCICTV
PEVSSVFIFPPKPKDVLTITLTPKVTCVVVDISKDDPEVQFSWFVDDVEV
HTAQTQPREEQFNSTFRSVSELPIMHQDWLNGKEFKCRVNSAAFPAPIEK
TISKTKGRPKAPQVYTIPPPKEQMAKDKVSLTCMITDFFPEDITVEWQWN
GQPAENYKNTQPIMDTDGSYFVYSKLNVQKSNWEAGNTFTCSVLHEGLHN
HHTEKSLSHSPGK-
```

The full sequence of the heavy chain variable region is as follows:

```
                                    (SEQ ID NO. 15)
QVQLKESGPGLVAPSQSLSITCTVSGFSLTTYGVSWVRQPPGKGLEWLGV
IWGDGNTNYHSALISRLSISKDNSKSQVFLKLNSLQTDDTATYYCAKGGP
YGNYVPFDYWGQGTTLTVSS
```

Each CDR and FR sequence in the heavy chain is as follows:

TABLE 2

| | |
|---|---|
| CDR-H1 | TYGVS (SEQ ID No. 1) |
| CDR-H2 | VIWGDGNTNYHSALIS (SEQ ID No. 2) |
| CDR-H3 | GGPYGNYVPFDY (SEQ ID No. 3) |
| FR-H1 | QVQLKESGPGLVAPSQSLSITCTVSGFSLT (SEQ ID No. 7) |
| FR-H2 | WVRQPPGKGLEWLG (SEQ ID No. 8) |
| FR-H3 | RLSISKDNSKSQVFLKLNSLQTDDTATYYCAK (SEQ ID No. 9) |
| FR-H4 | WGQGTTLTVSS (SEQ ID No. 10) |

The heavy chain coding sequence is as follows:

```
                                    (SEQ ID No. 20)
ATGGCTGTCCTGGCACTGCTCCTCTGCCTGGTGACATTCCCAAGCTGTGT
CCTGTCCCAGGTGCAGCTGAAGGAGTCAGGACCTGGCCTGGTGGCGCCCT
CACAGAGCCTGTCCATCACATGCACTGTCTCAGGGTTCTCATTAACCACC
TATGGTGTAAGCTGGGTTCGCCAGCCTCCAGGAAAGGGTCTGGAGTGGCT
GGGAGTAATATGGGGTGACGGGAACACAAATTATCATTCAGCTCTCATAT
CCAGACTGAGCATCAGCAAGGATAACTCCAAGAGCCAAGTTTTCTTAAAA
CTGAACAGTCTGCAAACTGATGACACAGCCACGTACTACTGTGCCAAAGG
AGGACCCTATGGTAACTACGTGCCCTTTGACTACTGGGGCCAAGGCACCA
CTCTCACAGTCTCCTCAGCCAAAACGACACCCCCATCTGTCTATCCACTG
GCCCCTGGATCTGCTGCCCAAACTAACTCCATGGTGACCCTGGGATGCCT
GGTCAAGGGCTATTTCCCTGAGCCAGTGACAGTGACCTGGAACTCTGGAT
CCCTGTCCAGCGGTGTGCACACCTTCCCAGCTGTCCTGCAGTCTGACCTC
TACACTCTGAGCAGCTCAGTGACTGTCCCCTCCAGCACCTGGCCCAGCGA
GACCGTCACCTGCAACGTTGCCCACCCGGCCAGCAGCACCAAGGTGGACA
AGAAAATTGTGCCCAGGGATTGTGGTTGTAAGCCTTGCATATGTACAGTC
CCAGAAGTATCATCTGTCTTCATCTTCCCCCCAAAGCCCAAGGATGTGCT
CACCATTACTCTGACTCCTAAGGTCACGTGTGTTGTGGTAGACATCAGCA
AGGATGATCCCGAGGTCCAGTTCAGCTGGTTTGTAGATGATGTGGAGGTG
CACACAGCTCAGACGCAACCCCGGGAGGAGCAGTTCAACAGCACTTTCCG
CTCAGTCAGTGAACTTCCCATCATGCACCAGGACTGGCTCAATGGCAAGG
AGTTCAAATGCAGGGTCAACAGTGCAGCTTTCCCTGCCCCCATCGAGAAA
ACCATCTCCAAAACCAAAGGCAGACCGAAGGCTCCACAGGTGTACACCAT
TCCACCTCCCAAGGAGCAGATGGCCAAGGATAAAGTCAGTCTGACCTGCA
TGATAACAGACTTCTTCCCTGAAGACATTACTGTGGAGTGGCAGTGGAAT
GGGCAGCCAGCGGAGAACTACAAGAACACTCAGCCCATCATGGACACAGA
TGGCTCTTACTTCGTCTACAGCAAGCTCAATGTGCAGAAGAGCAACTGGG
AGGCAGGAAATACTTTCACCTGCTCTGTGTTACATGAGGGCCTGCACAAC
CACCATACTGAGAAGAGCCTCTCCCACTCTCCTGGTAAATGA
```

The full sequence of the light chain of the obtained antibody is as follows:

```
                                        (SEQ ID No. 18)
METDTLLLWVLLLWVPGSTGDIVLTQSPASLAVSLGQRATISCRASESVD

SYGNSFMHWYQQKPGQPPKLLIYRASNLESGIPARFSGSGSRTDFTLTIN

PVEADDVATYYCQQSDEEPPTFGGGTNLEIKRADAAPTVSIFPPSSEQLT

SGGASVVCFLNNFYPKDINVKWKIDGSERQNGVLNSWTDQDSKDSTYSMS

STLTLTKDEYERHNSYTCEATHKTSTSPIVKSFNRNEC-
```

The full sequence of the light chain variable region is as follows:

```
                                        (SEQ ID NO. 16)
DIVLTQSPASLAVSLGQRATISCRASESVDSYGNSFMHWYQQKPGQPPKL

LIYRASNLESGIPARFSGSGSRTDFTLTINPVEADDVATYYCQQSDEEPP

TFGGGTNLEIK
```

Each CDR and FR sequence in the light chain is as follows:

TABLE 3

| | |
|---|---|
| CDR-L1 | RASESVDSYGNSFMH (SEQ ID No. 4) |
| CDR-L2 | RASNLES (SEQ ID No. 5) |
| CDR-L3 | QQSDEEPPT (SEQ ID No. 6) |
| FR-L1 | DIVLTQSPASLAVSLGQRATISC (SEQ ID No. 11) |
| FR-L2 | WYQQKPGQPPKLLIY (SEQ ID No. 12) |
| FR-L3 | GIPARFSGSGSRTDFTLTINPVEADDVATYYC (SEQ ID No. 13) |
| FR-L4 | FGGGTNLEIK (SEQ ID No. 14) |

The light chain coding sequence is as follows:

```
                                        (SEQ ID NO. 21)
ATGGAGACAGACACACTCCTGCTATGGGTGCTGCTGCTCTGGGTTCCAGG

TTCCACAGGTGACATTGTGCTGACCCAATCTCCAGCTTCTTTGGCTGTGT

CTCTAGGGCAGAGGGCCACCATATCCTGCAGAGCCAGTGAAAGTGTTGAT

AGTTATGGCAATAGTTTTATGCACTGGTACCAGCAGAAACCAGGACAGCC

ACCCAAACTCCTCATCTATCGTGCATCCAACCTAGAATCTGGGATCCCTG

CCAGGTTCAGTGGCAGTGGGTCTAGGACAGACTTCACCCTCACCATTAAT

CCTGTGGAGGCTGATGATGTTGCAACCTATTACTGTCAGCAGAGTGATGA

GGAGCCTCCGACGTTCGGTGGAGGCACCAACCTGGAAATCAAACGGGCTG

ATGCTGCACCAACTGTATCCATCTTCCCACCATCCAGTGAGCAGTTAACA

TCTGGAGGTGCCTCAGTCGTGTGCTTCTTGAACAACTTCTACCCCAAAGA

CATCAATGTCAAGTGGAAGATTGATGGCAGTGAACGACAAAATGGCGTCC
```

-continued

```
TGAACAGTTGGACTGATCAGGACAGCAAAGACAGCACCTACAGCATGAGC

AGCACCCTCACGTTGACCAAGGACGAGTATGAACGACATAACAGCTATAC

CTGTGAGGCCACTCACAAGACATCAACTTCACCCATTGTCAAGAGCTTCA

ACAGGAATGAGTGTTAG
```

EXAMPLE 2

Expression of Anti-ANGPTL3 Monoclonal Antibody (1) Construction of pTT5-IgG1 Plasmid:

The following sequence was obtained by gene synthesis:

```
                                        (SEQ ID No. 22)
gaattcgccgccaccatgggcgtgatcaagcccgacatgaagatcaagct

gaggatggagggcgcagtgaacggacacaagttcgtgatcgagggcgacg

gaaagggcaagcctttcgagggcaagcagaccatggacctgacagtgatc

gagggagctcctctgcctttcgcctacgacatcctgaccaccgtgttcga

ctacggcaaccgcgtgttcgccaagtaccccaaggacatccccgactact

tcaagcagaccttccccgagggctacagttgggaacggagcatgacctac

gaggaccagggcatttgcatcgccaccaacgacatcaccatgatgaaggg

cgtcgacgactgcttcgtgtacaagatccgcttcgacggcgtgaactttc

ccgctaacggccccgtgatgcagagaaagaccctcaagtgggagcccagc

accgagaagatgtacgtcagagacggagtgctgaagggagacgtgaacat

ggccctgctgctggaaggaggaggacactaccgctgcgacttcaagacca

cctacaaggccaagaaggtggtgcagctgcccgattaccacttcgtggac

caccggatcgagatcgtgtcccacgacaaggactacaacaaggtcaagct

gtacgagcacgccgaggctcatagcggactgcctagacaggcaggaggag

gaggatctatggccagcgccagcggaagcgataacggatcagcaggagga

ctgagaccttggccaggaccaggagcagcaggactggacgcagatgcagg

aggagcaggaggagacgcagcagcttcagtggccgccgctctgcagtcta

gaagaagagcagccggcgagacctacagcagaaaggagaagtctctgggc

ctcctctgcgagaacttcgtgaacctgtacggccagaccggctcagatgg

agcaggagcagcagcagacgcagacggacagcctagcgatatttgcctgg

acgccgcagctctgagactgcacgtgcctagaaggcggatctacgacatc

gtgaacgtgctggaggctctgggagtggtcgtgagaaaggccaagaaccg

gtacacttggaccggaacagcccacctggctacaacactggccgctctgg

ctacagcagcagcaagaggagacgcagacgacgatggagaactgatggac

ggagcaggagacggaggaggatctagcgacgacggagaaggaggagcctc

tcagacaccagcagctccaggaacagcagcagcagctctggcagctgtgg

tgacagtgtacaggctgaggaagagcgtggacaccaggaaggagaagagc

ctgggagtgctgagccagagattcgtgcagctcttcctgctgggcggaac

agagatgcctcctggagacgtgggaacaacatctagcgccgcagcaggag

ctccaggatctggacctagcggaggaggaggagtgggagatagcagcgtg

ggcgatacagcaggaatcgtggctccaggagccccaggcaatagatctag
```

-continued

```
cacaggcctggcagacggaggatctggaggagtggctaacggagcagacg
gaccaggaggatctatcgtgtctctggaagccgccgcagctagactgctg
ggaccttctgtgggagctacaccagcagcagtggccgccaaaatgaagac
caaggtccgccggctgtacgacatcgccaacatcctggccagcctgaaca
tcatcaagaaggtgcacaccgccagcaggaaacccgcttttcgctggctg
ggaccagctacacctcaggctccagctacagccggaagaagcacagcagg
agcagctctgacagtgccaggagctaacggcaagcctcccctgagacaca
gaaggcctagacctctgctgagactgctgccagctccaggcgacagaacc
cccacttgcagaagactgggcagaagcggaagaggcagcggatttggctg
cagacccacttgccagtgtagagcagatcctcctagactgctggctcagc
aggtcagacctagcagaccaggaacccacacegctagcaccaagggacct
agcgtgttccctctggctccttgtagcagaagcaccagcgagtctacagc
agctctgggttgcctggtgaaggactacttccccgagccagtgaccgtgt
cttggaacagcggagctctgaccagcggagtgcacacattcccagcagtg
ctgcagagcagcggactgtactctctgagcagcgtggtgaccgtgccttc
ttctagcctgggcaccaagacctacacttgcaacgtggaccacaagccca
gcaacaccaaggtggacaagcgggtggagagcaaatacggccctccttgc
cctccttgccctgctccagagtttctgggaggacctagcgtgttcctgtt
ccctcccaagcccaaggacaccctgatgatcagcaggacccccgaagtga
cttgcgtggtggtggacgtgtctcaggaggaccccgaggtgcagttcaat
tggtacgtggacggagtggaggtgcacaacgctaagaccaagcccaggga
ggagcagttcaacagcacctacagggtggtgtccgtgctgacagtggtgc
accaggattggctgaacggcaaggagtacaagtgcaaggtgtccaacaag
ggcctgcccagcagcatcgagaagaccatcagcaaggccaagggccagcc
tagaga
```

gaattc is the EcoRI restriction site, gctagc is the NheI restriction site, and ggatcc is the BamHI restriction site. The Stuffer sequence with a length of 2076 bp is between the EcoRI restriction site and the NheI restriction site, represented by --SS--. A longer Stuffer sequence facilitates the subsequent insertion of the DNA sequence of the antibody variable region. The synthesized DNA sequence was constructed into the pTT5 plasmid at the EcoRI and BamHI restriction sites by restriction enzyme digestion and ligation to obtain the pTT5-IgG1 plasmid.

(2) Construction of pTT5-KappaC Plasmid:

By gene synthesis, gaattc was added at the 5' end of SEQ ID No. 22, and the following sequence was added at the 3' end:

```
                                    (SEQ ID NO. 23)
gctagcgtggtgtgcctcctgaacaacttctaccccagggaggccaaggt
ccagtggaaggtggacaacgctctgcagagcggcaactctcaggagagcg
tgacagagcaggacagcaaggacagcacctacagcctgagcagcacactg
```

-continued

```
accctgtctaaggccgactacgagaagcacaaggtgtacgcttgcgaggt
gacccatcagggactgtctagcccagtgaccaagagcttcaaccgaggcg
agtgctaatgaggatcc
```

gaattc is the EcoRI restriction site, gctagc is the NheI restriction site, and ggatcc is the BamHI restriction site. The Stuffer sequence with a length of 2076 bp is between the EcoRI restriction site and the NheI restriction site, represented by --SS--. A longer Stuffer sequence facilitates the subsequent insertion of the DNA sequence of the antibody variable region. The synthesized DNA sequence was constructed into the pTT5 plasmid at the EcoRI and BamHI restriction sites by restriction enzyme digestion and ligation to obtain the pTT5-KappaC plasmid.

(3) Construction of Expression Plasmid in Mammalian Cells

Construction of expression vector of heavy chain of anti-ANGPTL3 monoclonal antibody: The expression plasmid pTT5-ANGPTL3-H of the heavy chain of the anti-ANGPTL3 antibody was constructed based on pTT5-IgG1. First, the signal peptide amino acid sequence was added to the N-terminus of the amino acid sequence of the heavy chain variable region of the anti-ANGPTL3 monoclonal antibody, and then converted into the DNA sequence suitable for expression in mouse CHO cells by using the COStar codon optimization software (ATGGGCTGGAGCTGCATCATCCTGTTCCTGGTGGCCACCGCCACCGGCGTGCACAGC, SEQ ID No. 24, was added to the N-terminus of SEQ ID No. 20). On the DNA sequence, the EcoRI restriction site (gaattc) and the Kozak sequence (gccgccacc) were added to the 5' end, and the NheI restriction site (gctagc) was added to the 3' end. The DNA sequence designed above was synthesized and constructed into the pTT5-IgG1 plasmid at the EcoRI restriction site and the NheI restriction site to obtain the pTT5-ANGPTL3-H plasmid that can express the heavy chain of the anti-ANGPTL3 antibody. The plasmid was amplified with *Escherichia coli* DH5α and then extracted, and the correctness of the pTT5-ANGPTL3-H-IgG1 engineering plasmid sequence was checked by gene sequencing.

Construction of expression vector of light chain of anti-ANGPTL3 antibody: The expression plasmid pTT5-ANGPTL3-L of the light chain of the anti-ANGPTL3 antibody was constructed based on pTT5-KappaC. First, the signal peptide amino acid sequence was added to the N-terminus of the light chain variable region of the anti-ANGPTL3 antibody, the sequence of the first 21 amino acids (ADAAPTVSIFPPSSEQLTSGG, SEQ ID No. 25) that codes the Kappa constant region was added to the C-terminus of the amino acid sequence (SEQ ID No. 21) of the light chain variable region of the anti-ANGPTL3 antibody, and then converted into the DNA sequence suitable for expression in mouse CHO cells by using the COStar codon optimization software (ATGGGCTGGAGCTGCATCATCCTGTTCCTGGTGGCCACCGCCACCGGCGTGCACAGC, SEQ ID No. 25, was added to the C-terminus). On the DNA sequence, the EcoRI restriction site (gaattc) and the Kozak sequence (gccgccacc) were added to the 5' end, and the NheI restriction site (gctagc) was added to the 3' end. The DNA sequence designed above was synthesized and constructed into the pTT5-KappaC plasmid at the EcoRI restriction site and the NheI restriction site to obtain the pTT5-ANGPTL3-L plasmid that can express the light chain of the anti-ANGPTL3 antibody.

(4) Transient Expression of Antibody

The antibody was expressed using the ExpiCHO-S transient transfection expression system. 20 mL expression system is used for small-scale expression, and 300 mL expression system is used for large-scale expression. Briefly, ExpiCHO-S cells were inoculated into a 20 mL or 300 mL expression system the day before transfection at a cell density of 3-4×10$^6$ cells/mL, and then cultured overnight at 37° C. at 175 rpm under 8% $CO_2$; the next day, the viable cell density and viability were determined, and the transfection can be carried out when the cell density is 7-10×10$^6$ cells/mL and the viability is 95-99%; and the cells were diluted to 6×10$^6$ cells/mL with a fresh and pre-warmed ExpiCHO expression medium and mixed by gently shaking the flask, and DNA and a transfection reagent were mixed and then slowly added in a swirling manner, shaking to mix uniformly, to obtain a culture medium with a total plasmid DNA amount of 1.0 ng/mL. The cells was cultured at 37° C. at 175 rpm under 8% $CO_2$ for 10 days, during which the cell density was monitored, and feeds were supplied on one day and five days after transfection, respectively. After 10 days, the supernatant of the cell medium was collected and centrifuged at 2000 rpm for 10 min, to collect a supernatant, and the supernatant was centrifuged at 10000 rpm for 20 min to collect a supernatant for purification.

EXAMPLE 3

Detection of Affinity of Anti-ANGPTL3 Monoclonal Antibody

Angptl3 was immobilized on a CM5 sensor chip (Biacore T200, BR18010468 (GE Healthercare)) at 25° C. with HBS-EP as a running buffer (10 mM HEPES, 150 mM NaCl, 3 mM EDTA, 0.05% P20, pH 7.4). Flow cells 1 and 4 were activated on the surface of the sensor chip with fresh and mixed NHS (50 mmol/L) and EDC (200 mmol/L) for 420 s (10 μL/min). Then, Angptl3 diluted in 10 mmol/L NaAC (pH 5.0) according objected into the flow cell 4 to achieve binding of about 852 Response Unit. In addition, Fc1 was set to blank. After the amine coupling reaction, 1 mol/L ethanolamine hydrochloride (pH 8.5) waccording tojected for 420 s to block the remaining active coupling sites on the chip surface.

The detection was carried out at 25° C. with HBS-EP as a running buffer. The anti-ANGPTL3 monoclonal antibody (prepared in Example 2) waccording tojected onto the surfaces of flow cells 1, 2, 3, and 4 as an association stage, and then the running buffer waccording tojected as a dissociation stage. The running configuration is shown in Table 4.

TABLE 4

| Immobilization | |
|---|---|
| Ligand | ANGPTL3 |
| Immobilization level (RU) | 852 |
| Flow rate (μL/min) | 10 |
| Association & dissociation | |
| Association contact time (s) | 180 |
| Dissociation contact time (s) | 600 |
| Flow rate (μL/min) | 30 |
| Sample concentration (nM) | 6.25, 12.5, 25, 50, 100, 200, 400, 800 |

Figure 2:
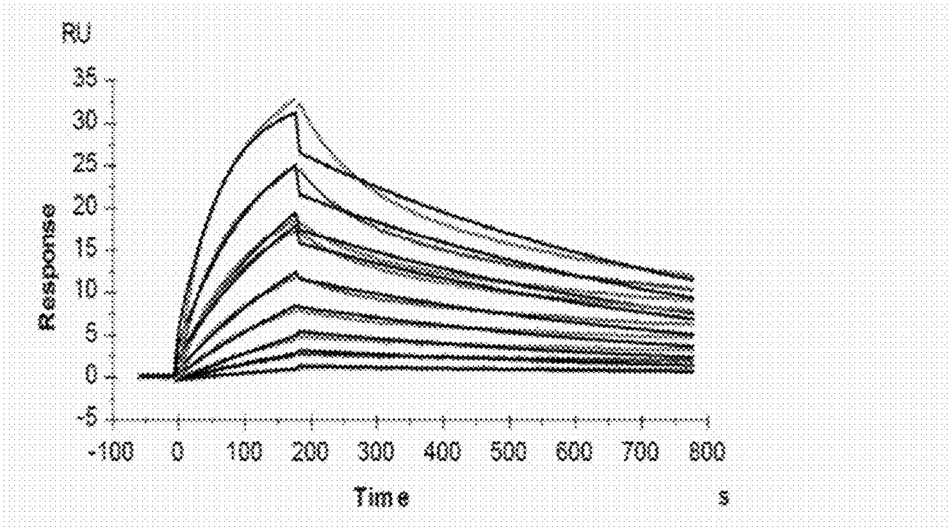
FIG. 2 shows the detection results of affinity of the anti-ANGPTL3 monoclonal antibody in Example 3 of the present invention.

All data were processed using Biacore T200 evaluation software version 3.1. The flow cell 1 was used as a double reference for the subtractive response unit. For the detection results of the affinity of the anti-ANGPTL3 antibody to the ANGPTL3 protein, refer to FIG. 2.

EXAMPLE 4

Anti-ANGPTL3 Monoclonal Antibody Blocks the Interaction Between ANGPTL3-FLD and Integrin αvβ3

Figure 3:
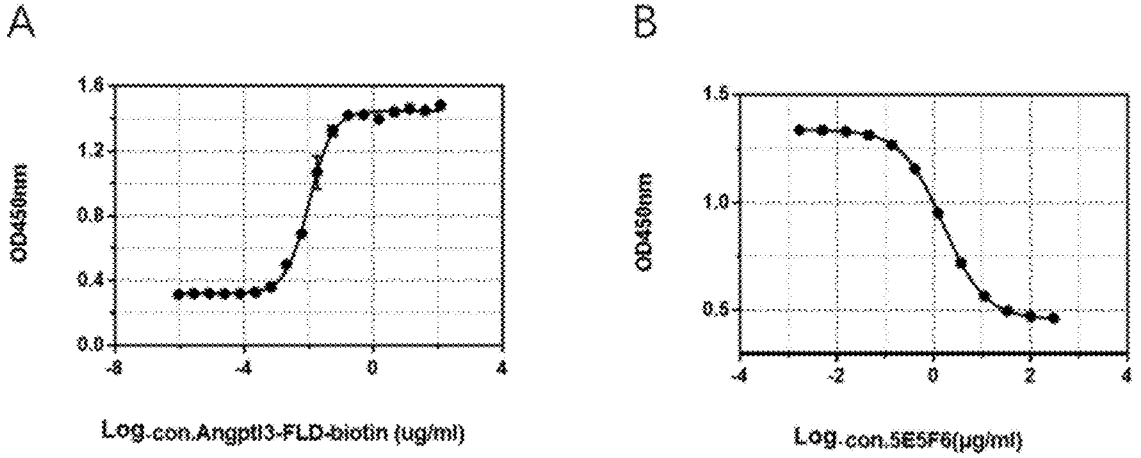
FIG. 3 shows the interaction between ANGPTL3-FLD and integrin αvβ3 blocked by the anti-ANGPTL3 monoclonal antibody in Example 4 of the present invention, wherein A is a curve of the binding of ANGPTL3-FLD to integrin αvβ3 detected by ELISA; and B shows the activity of the anti-ANGPTL3 antibody to block the binding of ANGPTL3-FLD to integrin αvβ3 detected by competitive ELISA.

Integrin αvβ3 is a key receptor for ANGPTL3-FLD to act on podocytes and mediate podocyte damage. Therefore, in order to evaluate the biological activity of the anti-ANGPTL3 monoclonal antibody, a competitive ELISA experiment was designed to evaluate the activity of the anti-ANGPTL3 monoclonal antibody blocking the interaction between ANGPTL3-FLD and integrin αvβ3. In the competitive experiment of the anti-ANGPTL3 monoclonal antibody blocking the interaction between ANGPTL3-FLD and integrin αvβ3, ANGPTL3-FLD was biotin-labeled, and the lowest saturated concentration of ANGPTL3-FLD-biotin binding to integrin αvβ3 was determined as 0.16 μg/mL by ELISA (as shown in FIG. 3A). The anti-ANGPTL3 monoclonal antibody was serially diluted with 0.16 μg/mL ANGPTL3-FLD-biotin solution as a diluent to obtain a series of concentrations. Theoretically, ANGPTL3-FLD-biotin can saturate integrin αvβ3 on a solid support in the absence of monoclonal antibody. However, when the epitope of ANGPTL3-FLD recognized by the monoclonal antibody overlaps with the epitope of ANGPTL3-FLD binding to integrin αvβ3, the antibody may compete with integrin αvβ3 for binding to ANGPTL3-FLD-biotin, so that ANGPTL3-FLD-biotin cannot bind to integrin αvβ3 on the solid support. As shown in FIG. 3B, the anti-ANGPTL3 monoclonal antibody can effectively block the interaction between ANGPTL3-FLD-biotin and integrin αvβ3, with EC50 of 1.57 μg/mL.

The experimental steps involved are as follows:

1. Plot a Curve of the Binding of Integrin αvβ3/ANGPTL3

(1) Integrin αvβ3 recombinant protein (R&D, 3050-AV-050) was diluted with a coating solution (a. 50 mM carbonate buffer with pH 9.6: $Na_2CO_3$ 1.59 g, $NaHCO_3$ 2.63 g, and distilled water to 1 L) to 1 μg/mL, and then added into an enzyme-linked plate in 100 μL per well, and then the enzyme-linked plate was placed in a wet box at 4° C. overnight.

(2) ANGPTL3-Biotin (the amino acid sequence of ANGPTL3 protein was set forth in SEQ ID No. 19, and the biotinylation of the protein was carried out by Beijing Jiaxuan) was diluted to 48 μg/mL with 1×PBS, and then diluted 3-fold to obtain a total of 12 concentrations. The diluted solution was added into an enzyme-linked plate in 100 μL per well, and then the enzyme-linked plate was placed in a wet box at 37° C. to react for 1 h.

(3) The enzyme-linked plate was washed three times, and then the Peroxidase-Labeled Streptavidin (1:4000) was added into the enzyme-linked plate to react at room temperature for 45 min. The enzyme-linked plate was washed five times, and then 100 μL of TMB chromogenic solution was added into the enzyme-linked plate to react for 3 min, the reaction was stopped with 100 μL of 2N $H_2SO_4$ (1 mol/L), and the reading at 450 nm was taken by an ELISA reader.

(4) A curve of the binding of integrin αvβ3/ANGPTL3 was plotted with the concentration of ANGPTL3-Biotin as horizontal coordinates and the OD value as vertical coordinates, and the lowest saturated concentration of integrin αvβ3 binding to ANGPTL3 was selected to carry out the antibody blocking experiment.

2. Detect a Half-Maximal Inhibitory Concentration of Anti-ANGPTL3-FLD mAb (1) Dilution with coating solution: Integrin αvβ3 was diluted with a coating solution to 1 μg/mL, and then added into an enzyme-linked plate in 100 μL per well, and then the enzyme-linked plate was placed in a wet box at 4° C. overnight.

(2) The enzyme-linked plate was washed three times, blocked with 0.5% BSA in 200 μL per well, and then placed in the wet box at 37° C. for 1 h.

(3) Biotin-ANGPTL3-FLD was diluted to 0.16 μg/mL with 1×PBS. The anti-ANGPTL3 monoclonal antibody (prepared in Example 2) was diluted to 500 μg/mL with the foregoing solution as a diluent, and then diluted 3-fold to obtain a total of 12 concentrations. The diluted solution was added into an enzyme-linked plate in 100 μL per well, and then the enzyme-linked plate was placed in a wet box at 37° C. to react for 1 h.

(4) The enzyme-linked plate was washed three times, and then the Biotin-Anti-ANGPTL3 polyclonal antibody (0.2 μg/mL) (R&D, BAF3829) was added into the enzyme-linked plate to react in a wet box at 37° C. for 1 h.

(5) The enzyme-linked plate was washed three times, and then the Peroxidase-Labeled Streptavidin (1:4000) was added into the enzyme-linked plate to react at room temperature for 45 min.

(6) The enzyme-linked plate was washed five times, and then 100 μL of TMB chromogenic solution was added into the enzyme-linked plate to react for 3 min, the reaction was stopped with 100 μL of $H_2SO_4$ (1 mol/L), and the reading at 450 nm was taken by an ELISA reader.

(7) A curve of the binding was plotted with the concentration of the antibody as horizontal coordinates and the OD value as vertical coordinates, to calculate the half-maximal inhibitory concentration of the antibody.

EXAMPLE 5

Anti-ANGPTL3 Monoclonal Antibody Alleviates Proteinuria in Mice with Adriamycin (ADR) Nephropathy 75 BALB/c mice (male, 6-8 weeks old, average weight 25 g) were randomly divided into a 4-week group and an 8-week group according to the observation time. 4-week group: control group (Ctrl), ADR group (modeling with a single tail vein injection of 10.5 mg/kg ADR), ADR+10 mg/kg 5E5F6 group (ADR+10 mg/kg mAb group), ADR+20 mg/kg 5E5F6 group (ADR+20 mg/kg mAb group, mAb is the anti-ANGPTL3 monoclonal antibody prepared in Example 2, the same below), ADR+40 mg/kg 5E5F6 group (ADR+40 mg/kg mAb group), and ADR+non-specific IgG group (ADR+ns-IgG group, the dose of ns-IgG (Shanghai Yisheng Biotechnology Co., Ltd., 36111ES10) corresponds to the dose of mAb, a total of 3 groups). 8-week group: Ctrl group, Ctrl+20 mg/kg mAb group, ADR group, ADR+20 mg/kg mAb group, and ADR+ns-IgG group. Different doses of anti-ANGPTL3 monoclonal antibody (prepared in Example 2) and corresponding doses of ns-IgG were intraperitoneally injected on the first day after modeling, the injecting performed once every 4 days until the end of observation. The protective effect of the intervention of the anti-ANGPTL3 monoclonal antibody on the podocyte damage and proteinuria in mice with ADR nephropathy. The urine was collected before modeling and at 1 week, 2 weeks, 3 weeks, 4 weeks, 6 weeks, and 8 weeks after modeling, and the urine albumin level of mice was detected by using a mouse albumin ELISA kit (Chondrex, #3012). The results for the 4-week group are shown in FIG. 4, and the results for the 8-week group are shown in FIG. 5.

Figure 4:
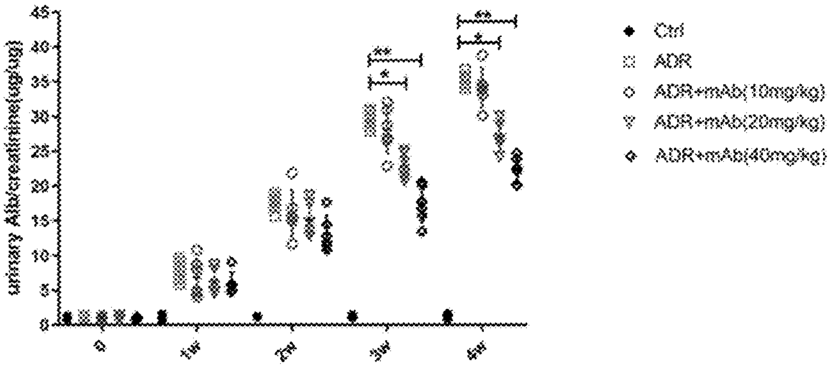
FIG. 4 shows the results of the intervention of the anti-ANGPTL3 monoclonal antibody in Example 5 of the present invention to reduce the urinary protein in an Adriamycin (ADR) nephropathy model (observed for 4 weeks) mice.
Figure 5:
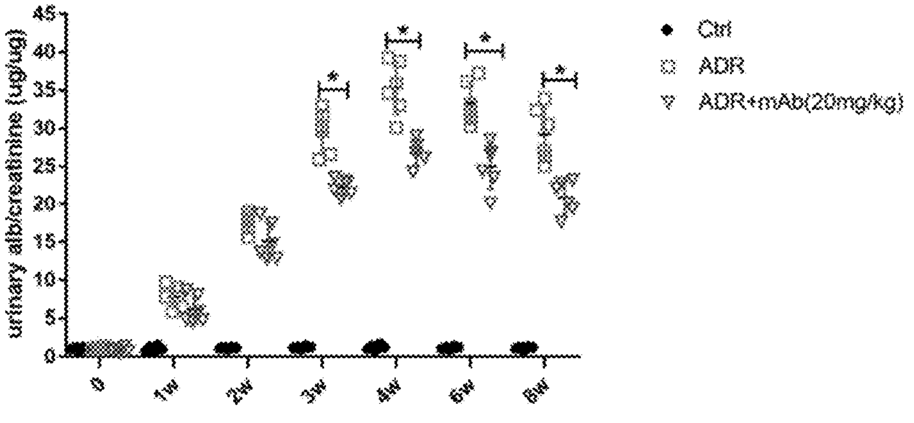
FIG. 5 shows the results of the intervention of the anti-ANGPTL3 monoclonal antibody in Example 5 of the present invention to reduce the urinary protein in an Adriamycin (ADR) nephropathy model (observed for 8 weeks) mice.

It can be learned from FIG. 4 (observed for 4 weeks) and FIG. 5 (observed for 8 weeks) that different doses of anti-ANGPTL3 monoclonal antibody has a significant effect on alleviating proteinuria in mice with ADR nephropathy.

Anti-ANGPTL3 Monoclonal Antibody Alleviates Hypoalbuminemia in Mice with Adriamycin (ADR) Nephropathy Mice in each group were sacrificed 4 weeks and 8 weeks after the ADR modeling, the serum of the mice was collected, and the serum albumin level of the mice was detected by ELISA. The results for the 4-week group are shown in FIG. 6, and the results for the 8-week group are shown in FIG. 7.

Figure 6:
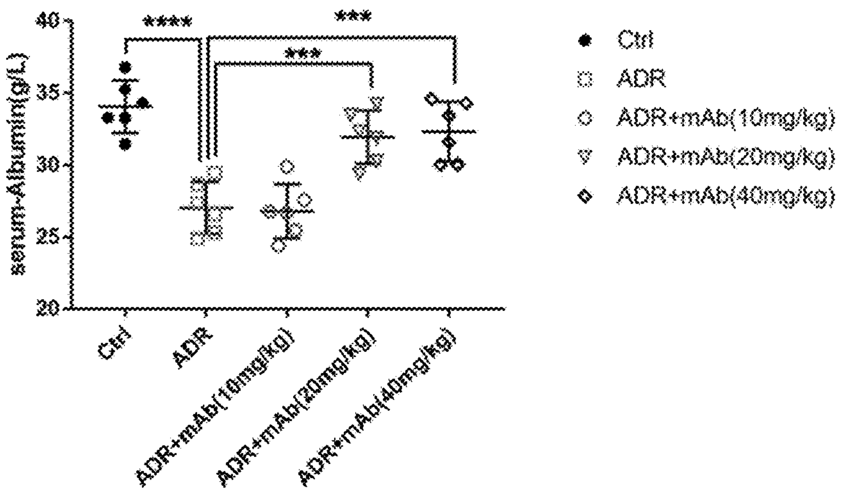
FIG. 6 shows the results of the intervention of the anti-ANGPTL3 monoclonal antibody in Example 5 of the present invention to alleviate the hypoalbuminemia in an Adriamycin (ADR) nephropathy model (observed for 4 weeks) mice.
Figure 7:
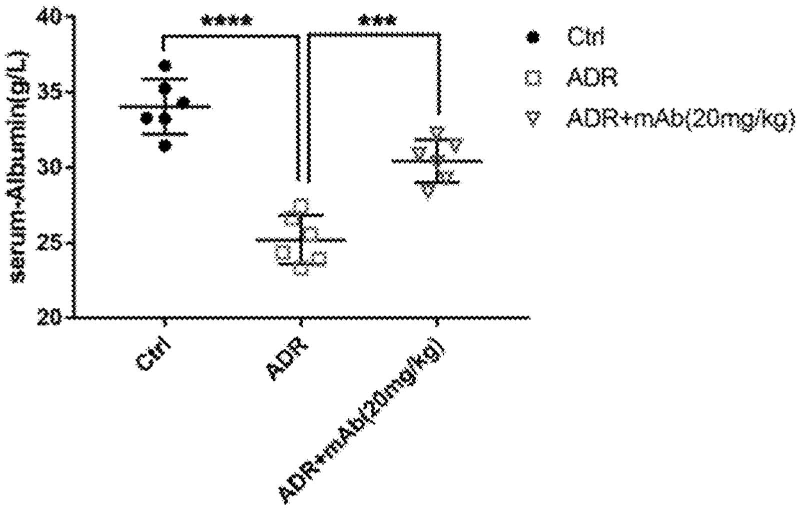
FIG. 7 shows the results of the intervention of the anti-ANGPTL3 monoclonal antibody in Example 5 of the present invention to alleviate the hypoalbuminemia in an Adriamycin (ADR) nephropathy model (observed for 8 weeks) mice.

It can be learned from FIG. 6 and FIG. 7 that different doses of anti-ANGPTL3 monoclonal antibody has a significant effect on alleviating hypoalbuminemia in mice with ADR nephropathy.

Anti-ANGPTL3 Monoclonal Antibody Alleviates Hypercholesterolemia in Mice with Adriamycin (ADR) Nephropathy Mice in each group were sacrificed 4 weeks and 8 weeks after the ADR modeling, the serum of the mice was collected, and the serum cholesterol level of mice was detected by the high iron-sulfuric acid chromogenic method (NanJing JianCheng Bioengineering Institute, article number: A111-1). The results for the 4-week group are shown in FIG. 8, and the results for the 8-week group are shown in 9.

Figure 8:
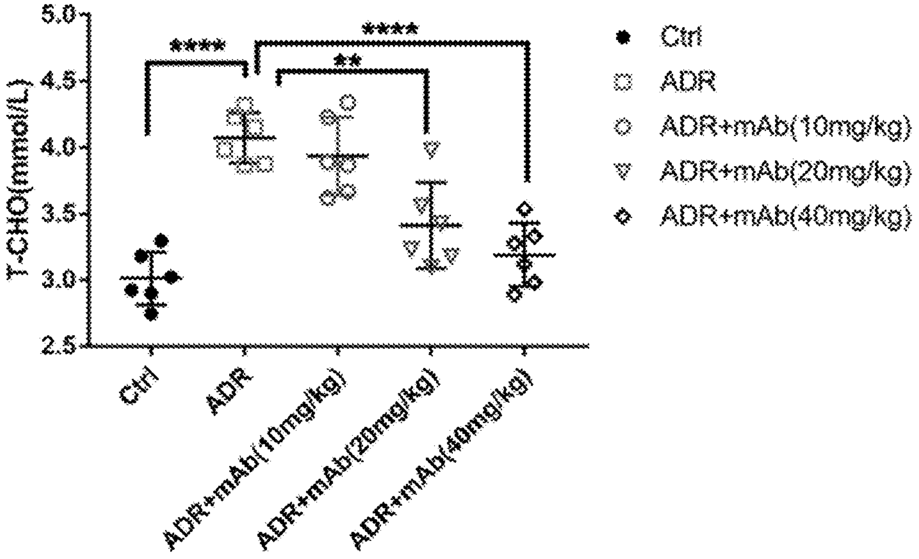
FIG. 8 shows the results of the intervention of the anti-ANGPTL3 monoclonal antibody in Example 5 of the present invention to alleviate the hypercholesterolemia in an Adriamycin (ADR) nephropathy model (observed for 4 weeks) mice.
Figure 9:
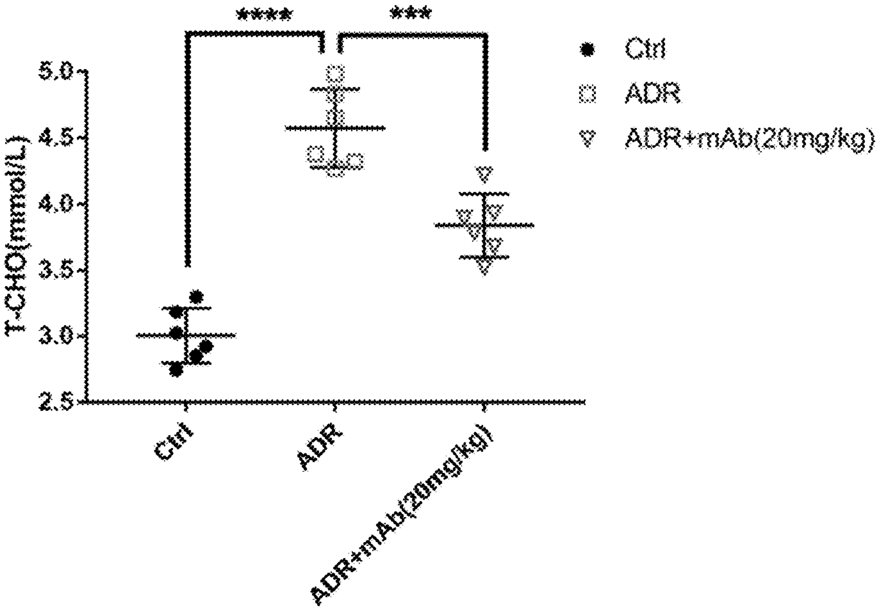
FIG. 9 shows the results of the intervention of the anti-ANGPTL3 monoclonal antibody in Example 5 of the present invention to alleviate the hypercholesterolemia in an Adriamycin (ADR) nephropathy model (observed for 8 weeks) mice.

It can be learned from FIG. 8 and FIG. 9 that different doses of anti-ANGPTL3 monoclonal antibody has a significant effect on alleviating hypercholesterolemia in mice with ADR nephropathy.

Figure 10:
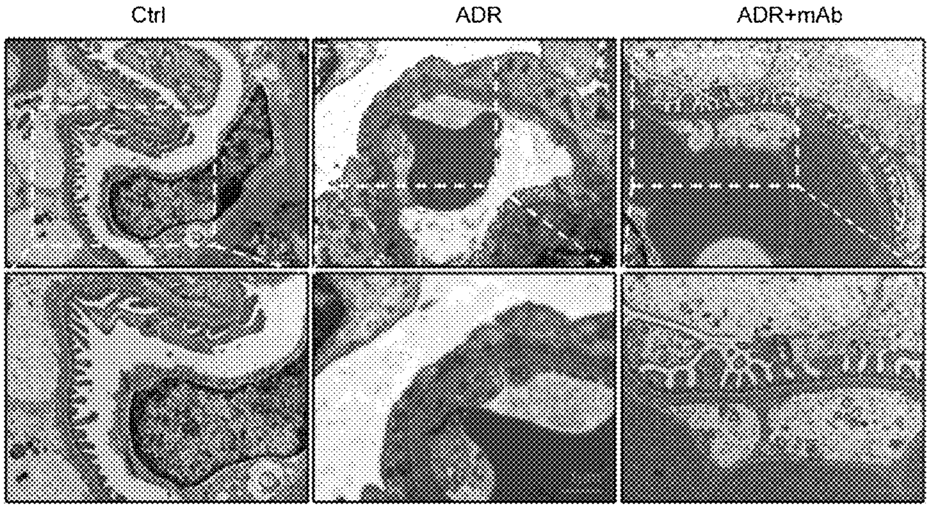
FIG. 10 shows that the anti-ANGPTL3 monoclonal antibody in Example 5 of the present invention alleviating the podocyte damage in an Adriamycin (ADR) nephropathy model mice.

Anti-ANGPTL3 Monoclonal Antibody Alleviates Kidney Tissue Damage in Mice with Adriamycin (ADR) Nephropathy Mice in each group were sacrificed 8 weeks after the ADR modeling, and the kidney tissue of the mice was collected. A 1 $mm^3$ tissue block was fixed with 2.5% glutaraldehyde solution for 2 h or more, and then rinsed with 0.1 mol/L phosphate buffer for 15 min with a total of 3 times. The tissue block was fixed with 1% osmium tetroxide for 2-3 h, and then rinsed with phosphate buffer for 3 times. The tissue block was immersed in 4° C. pre-cooled 50% ethanol, 70% ethanol, 90% ethanol, a mixture of 90% ethanol and 90% acetone (1:1), and 90% acetone for 15-20 min, successively, and then immersed in 100% acetone at room temperature for 15 min with a total of 3 times. The tissue block was then embedded in a mixture of pure acetone and an embedding medium (2:1) and left at room temperature for 3-4 h, then embedded in a mixture of acetone and the embedding medium (1:2) overnight, and finally immersed in the embedding agent at 37° C. for 2-3 h. After cured in a 60° C. oven for 48 h, it waccording to position for sectioning. A 60-80 nm ultrathin section was obtained and placed on copper grids, stained with 3% uranyl acetate-lead citrate, and observed with TEM to form an image. It can be seen from the image of the kidney tissue in the ADR group formed by TEM that the extensive fusion of foot processes of podocytes disappears, the podocyte damage in the kidney tissue of the mice in the ADR+20 mg/kg mAb group is significantly alleviated compared with the ADR group, and the shape of the foot processes of the mice in the ADR+20 mg/kg mAb group basically returns to normal (as shown in FIG. 10).

Anti-ANGPTL3 Monoclonal Antibody Reduces the Activation of PAN-Induced Podocyte Surface Integrin αvβ3

Human podocyte lines were cultured in vitro, and podocytes that differentiated to 12-14 days in good condition were selected. The podocytes were divided into the following groups: a negative control group, incubated with no antibody; a control group, no intervention with PAN and ANGPTL3 monoclonal antibody; a PAN group, intervention with 50 μg/mL PAN alone for 48 h; and an anti-ANGPTL3 monoclonal antibody group (100 ng/mL): pre-intervention with 100 ng/mL anti-ANGPTL3 monoclonal antibody (prepared in Example 2) for 1 h, and then intervention with 50 μg/mL PAN for 48 h.

After the intervention with PAN for 48 h, the podocytes were digested with 0.25% pancreatin, the digestion was terminated in a complete medium, and the cells were resuspended. The cells were washed twice with pre-cooled PBS, and waste liquid was discarded. The cells were incubated with the Anti-Integrin $\alpha v\beta 3$ antibody (1:100) (Kerafast, US, #EBW107) at room temperature for 60 min. After the incubation, the cells were washed three times with pre-cooled PBS. The cells were incubated with the Goat Anti-Mouse IgG(H+L) FITC-conjugated antibody (1:200) (Affinity, US, #S0007) at room temperature for 60 min in the dark. After the incubation, the cells were washed three times with pre-cooled PBS. The cell suspension (300 μL) in each group was transferred into a flow tube, and the cells in each group were detected by using a flow cytometer.

Figure 11:
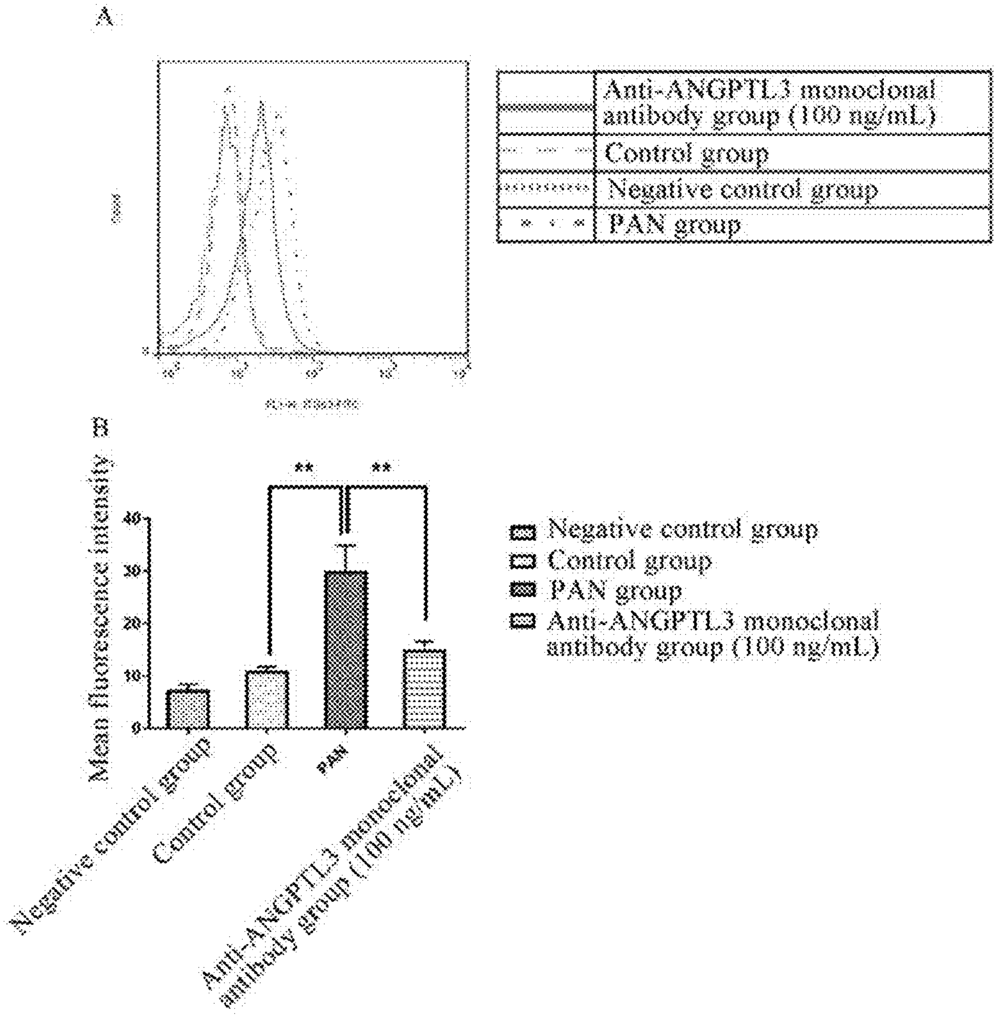
FIG. 11 shows the results that the anti-ANGPTL3 monoclonal antibody in Example 5 of the present invention reducing the activation of PAN-induced podocyte surface integrin αvβ3.

The activation of podocyte surface integrin $\alpha v\beta 3$ in each group was detected by flow cytometry. The results show that, compared with the control group, the activation of podocyte surface integrin $\alpha v\beta 3$ in the PAN group is significantly increased ($P<0.05$). As shown in FIG. 11A and FIG. 11B, compared with the PAN group, the activation of podocyte surface integrin $\alpha v\beta 3$ in the anti-ANGPTL3 monoclonal antibody group (100 ng/mL) is significantly reduced ($P<0.05$).

Anti-ANGPTL3 Monoclonal Antibody Reduces the Apoptosis of PAN-Induced Podocyte

Human podocyte lines were cultured in vitro, and podocytes that differentiated to 12-14 days in good condition were selected. The podocytes were divided into the following groups: a control group, no intervention with PAN and ANGPTL3 monoclonal antibody; a PAN group, intervention with 50 μg/mL PAN alone for 48 h; an anti-ANGPTL3 monoclonal antibody group (100 ng/mL): pre-intervention with 100 ng/mL anti-ANGPTL3 monoclonal antibody for 1 h, and then intervention with 50 μg/mL PAN for 48 h; and an anti-ANGPTL3 monoclonal antibody group (500 ng/mL): pre-intervention with 500 ng/mL anti-ANGPTL3 monoclonal antibody for 1 h, and then intervention with 50 μg/mL PAN for 48 h.

After the intervention with PAN for 48 h, the podocytes were digested with 0.25% pancreatin, the digestion was terminated in a complete medium, and the cells were resuspended. The cells were washed twice with pre-cooled PBS, and waste liquid was discarded. The cells were adjusted to a concentration of $1\times10^6$ cells/mL with 1×Binding Buffer. 100 μL of cell suspension (containing $1\times10^5$ cells) was transferred into a 5 mL centrifuge tube and then 5 μL of PE-Annexin V and 5 μL of 7-AAD were added, mixing uniformly, and then incubated at room temperature (25° C.) for 15 min in the dark. After the incubation, the cells were transferred into a flow tube, and 400 μL of 1×Binding Buffer was then added. The cells in each group were analyzed by using a flow cytometer within 1 h.

Figure 12:
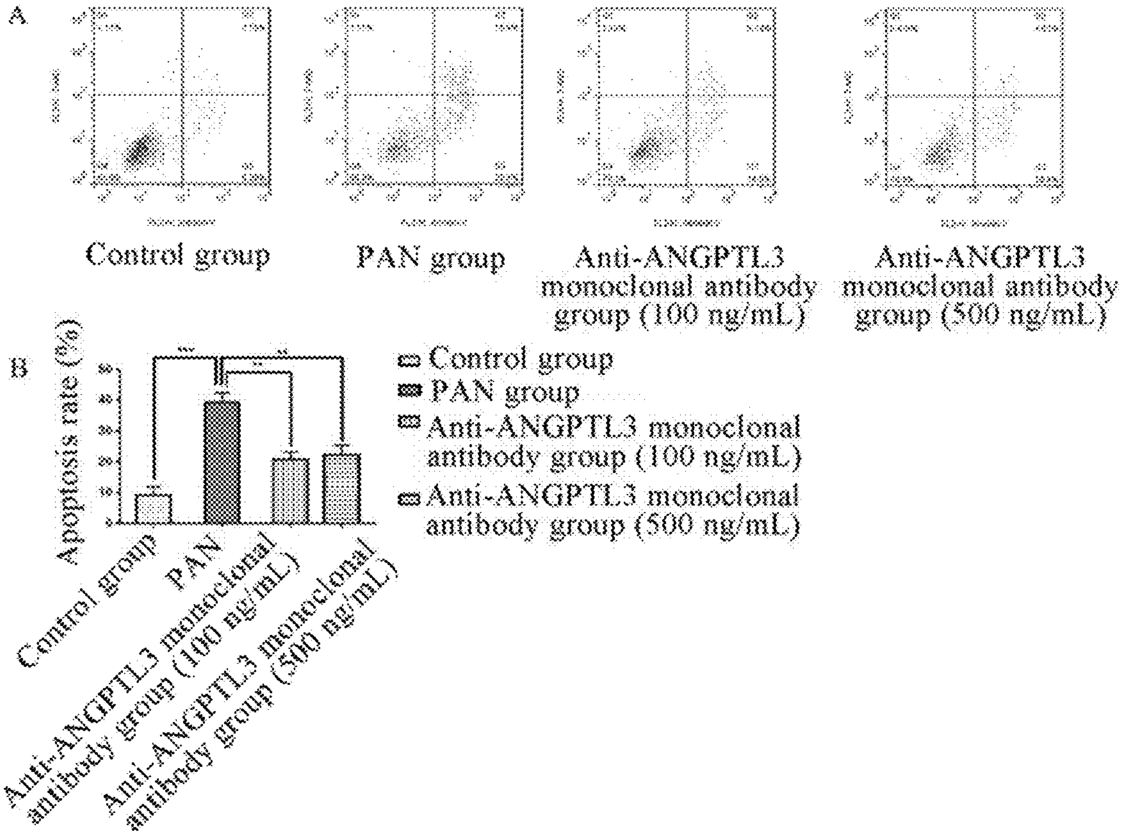
FIG. 12 shows the results that the anti-ANGPTL3 monoclonal antibody in Example 5 of the present invention reducing the apoptosis of PAN-induced podocyte.

The apoptosis of podocytes in different groups was detected by PE-Annexin-V/7-AAD staining (BD, US, PE Annexin-V Apoptosis Detection Kit I (#559763)). The results show that, compared with the control group, the apoptosis rate of the PAN group is significantly increased ($P<0.05$). As shown in FIG. 12A and FIG. 12B, compared with the PAN group, the apoptosis rates of the anti-ANGPTL3 monoclonal antibody group (100 ng/mL) and the anti-ANGPTL3 monoclonal antibody group (500 ng/mL) are significantly reduced ($P<0.05$).

In conclusion, the present invention effectively overcomes various disadvantages in the prior art, and has a high industrial utilization value.

The above embodiments merely exemplify the principles and effects of the present invention, but are not intended to limit the present invention. A person skilled in the art can modify or change the above embodiments without departing from the spirit and scope of the present invention. Therefore, all equivalent modifications or changes made by a person of ordinary skill in the art without departing from the spirit and technical idea of the present invention shall be covered by the claims of the present invention.

What is claimed is:

1. An anti-ANGPTL3 antibody or an antigen-binding fragment thereof, comprising a heavy chain variable region and a light chain variable region, wherein the heavy chain variable region comprises complementarity determining regions, comprising CDR-H1 having an amino acid sequence as set forth in SEQ ID No. 1, CDR-H2 having an amino acid sequence as set forth in SEQ ID No. 2, and CDR-H3 having an amino acid sequence as set forth in SEQ ID No. 3; and the light chain variable region comprises complementarity determining regions, comprising CDR-L1 having an amino acid sequence as set forth in SEQ ID No. 4, CDR-L2 having an amino acid sequence as set forth in SEQ ID No. 5, and CDR-L3 having an amino acid sequence as set forth in SEQ ID No. 6.

2. The anti-ANGPTL3 antibody or the antigen-binding fragment thereof according to claim 1, wherein the anti-ANGPTL3 antibody or the antigen-binding fragment thereof can bind to a fibrinogen-like domain (FLD) of ANGPTL3;

and/or the anti-ANGPTL3 antibody or the antigen-binding fragment thereof can specifically recognize ANGPTL3;

and/or the anti-ANGPTL3 antibody or the antigen-binding fragment thereof is a monoclonal antibody;

and/or the anti-ANGPTL3 antibody or the antigen-binding fragment thereof is derived from mouse;

and/or the anti-ANGPTL3 antibody or the antigen-binding fragment thereof is humanized.

3. The anti-ANGPTL3 antibody or the antigen-binding fragment thereof according to claim 1, further comprising a framework region (FR), wherein the framework region of the heavy chain variable region comprises FR-H1 having an amino acid sequence as set forth in SEQ ID No. 7, FR-H2 having an amino acid sequence as set forth in SEQ ID No. 8, FR-H3 having an amino acid sequence as set forth in SEQ ID No. 9, and FR-H4 having an amino acid sequence as set forth in SEQ ID No. 10; and the framework region of the light chain variable region comprises FR-L1 having an amino acid sequence as set forth in SEQ ID No. 11, FR-L2 having an amino acid sequence as set forth in SEQ ID No. 12, FR-L3 having an amino acid sequence as set forth in SEQ ID No. 13, and FR-L4 having an amino acid sequence as set forth in SEQ ID No. 14.

4. The anti-ANGPTL3 antibody or the antigen-binding fragment thereof according to claim 1, wherein the heavy chain variable region having:

a) an amino acid sequence as set forth in SEQ ID No. 15; or b) an amino acid sequence having at least 80% sequence identity with SEQ ID No. 15 and having the same function as the amino acid sequence in a).

5. The anti-ANGPTL3 antibody or the antigen-binding fragment thereof according to claim 1, wherein the light chain variable region having:

c) an amino acid sequence as set forth in SEQ ID No. 16; or d) an amino acid sequence having at least 80% sequence identity with SEQ ID No. 16 and having the same function as the amino acid sequence in c).

6. The anti-ANGPTL3 antibody or the antigen-binding fragment thereof according to claim 1, wherein the anti-ANGPTL3 antibody or the antigen-binding fragment thereof comprises a heavy chain having an amino acid sequence as set forth in SEQ ID No. 17;

and/or the anti-ANGPTL3 antibody or the antigen-binding fragment thereof comprises a light chain having an amino acid sequence as set forth in SEQ ID No. 18.

7. The anti-ANGPTL3 antibody or the antigen-binding fragment thereof according to claim 1, wherein the anti-ANGPTL3 antibody or the antigen-binding fragment thereof is selected from the group consisting of a Fab' fragment, a F(ab')2 fragment, a bispecific Fab dimer, a trispecific Fab trimer, Fv, a single-chain Fv protein, bis-scFv, (scFv)2, a minibody, a diabody, a tribody, a tetrabody, a disulfide-stabilized Fv protein, or a single-domain antibody.

8. A pharmaceutical composition, comprising the anti-ANGPTL3 antibody or the antigen-binding fragment thereof according to claim 1 and a pharmaceutically acceptable carrier.

9. A kit for detection, comprising the anti-ANGPTL3 antibody or the antigen-binding fragment thereof according to claim 1.

10. The pharmaceutical composition of claim 8, wherein the pharmaceutical composition is for use in the treatment of proteinuria, hypoalbuminemia, and hypercholesterolemia.

* * * * *